United States Patent
Swerdlow et al.

(10) Patent No.: US 11,952,337 B2
(45) Date of Patent: *Apr. 9, 2024

(54) BIOENERGETICALLY ACTIVE ESTERS FOR HEALTH AND DISEASE

(71) Applicant: University of Kansas, Lawrence, KS (US)

(72) Inventors: Russell Swerdlow, Leawood, KS (US); Laird Forrest, Lawrence, KS (US); Jordan Hunt, Lawrence, KS (US); Heather Wilkins, Kansas City, KS (US); Eli Michaelis, Lawrence, KS (US)

(73) Assignee: University of Kansas, Lawrence, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/745,773

(22) Filed: May 16, 2022

(65) Prior Publication Data
US 2023/0109376 A1 Apr. 6, 2023

Related U.S. Application Data

(63) Continuation of application No. 17/280,235, filed as application No. PCT/US2019/053901 on Sep. 30, 2019, now Pat. No. 11,332,432.

(60) Provisional application No. 62/739,275, filed on Sep. 30, 2018.

(51) Int. Cl.
*C07C 69/716* (2006.01)
*A61P 25/28* (2006.01)

(52) U.S. Cl.
CPC .......... *C07C 69/716* (2013.01); *A61P 25/28* (2018.01)

(58) Field of Classification Search
CPC .............................. C07C 69/716; A61P 25/28
See application file for complete search history.

(56) References Cited

U.S. PATENT DOCUMENTS

| 11,332,432 B2 * | 5/2022 | Swerdlow | C07C 69/716 |
| 2005/0271739 A1 | 12/2005 | Wang | |
| 2008/0176881 A1 | 7/2008 | Michellys et al. | |
| 2008/0279786 A1 | 11/2008 | Cash | |

OTHER PUBLICATIONS

International Search Report and Written Opinion for PCT Appl. Ser. No. PCT/US2019/053901 dated Dec. 6, 2019 (6 pages).
U.S. Notice of Allowance on U.S. Appl. No. 17/280,235 dated Jan. 20, 2022 (5 pages).

* cited by examiner

*Primary Examiner* — Deborah D Carr
(74) *Attorney, Agent, or Firm* — Foley & Lardner LLP

(57) ABSTRACT

Compounds, compositions, and methods related to bioenergetic metabolism are provided. The compounds and compositions are suited to promote bioenergetic processes including cellular respiration and glycolytic flux and may be used to treat mitochondrial disorders, neurodegenerative diseases (such as Alzheimer's disease (AD), Parkinson's disease, and/or amyotrophic lateral sclerosis), multiple sclerosis, and/or epilepsy.

14 Claims, 13 Drawing Sheets

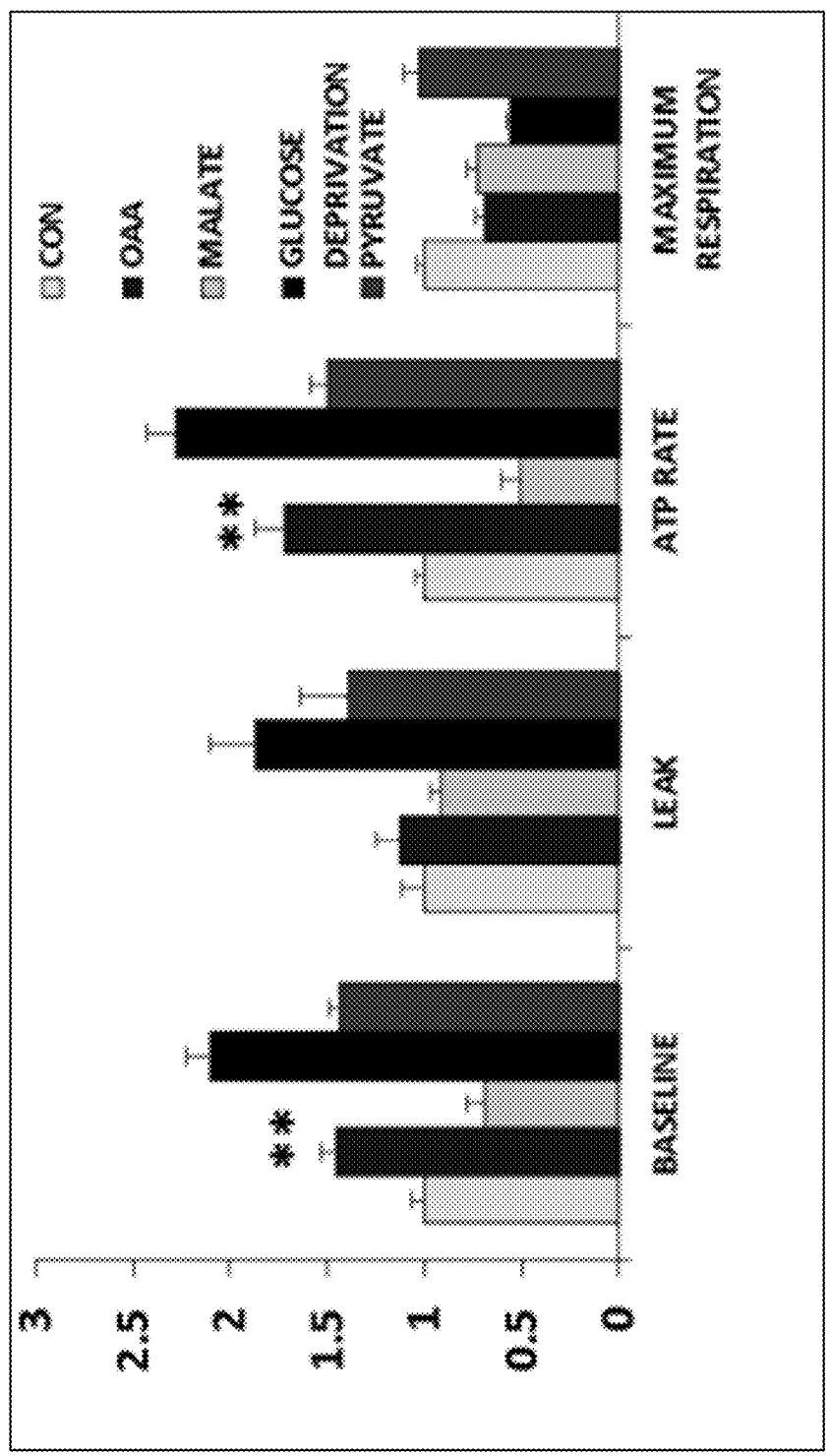

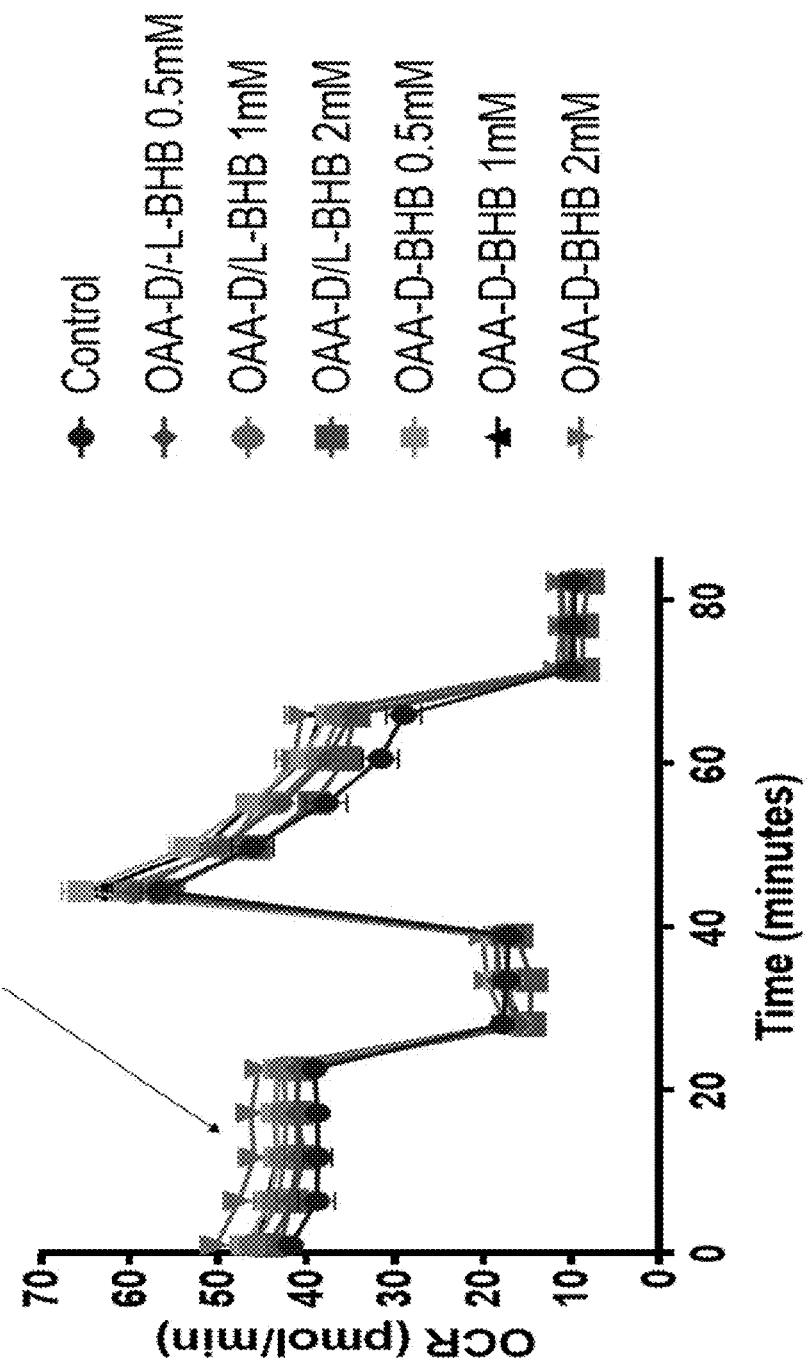

BIOENERGETICALLY ACTIVE ESTERS FOR HEALTH AND DISEASE

CROSS-REFERENCE TO RELATED APPLICATIONS

This application is a continuation of U.S. patent application Ser. No. 17/280,235, filed on Mar. 26, 2021, which is a U.S. National Phase Application under 35 U.S.C. § 371 of International Application No. PCT/US2019/053901, filed on Sep. 30, 2019, which claims priority under 35 U.S.C. § 119(e) to U.S. Provisional Application 62/739,275, filed on Sep. 30, 2018, the entire contents of which are incorporated herein by reference.

STATEMENT OF FEDERALLY FUNDED RESEARCH

This invention was made with government support under NS077852 and AG060817 awarded by the National Institutes of Health. The government has certain rights in the invention.

FIELD

The present technology is directed to compounds, compositions, and methods useful in modulating bioenergetic metabolism. For example, this technology is particularly suited to promote bioenergetic processes including cellular respiration and glycolytic flux. Accordingly, the compounds and compositions may be used to treat neurodegenerative diseases such as Alzheimer's disease (AD).

SUMMARY

In an aspect, a compound of Formula I is provided:

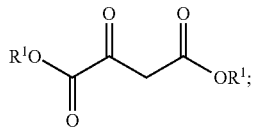

(I)

or a pharmaceutically acceptable salt and/or solvate thereof, wherein both $R^1$ are selected from:

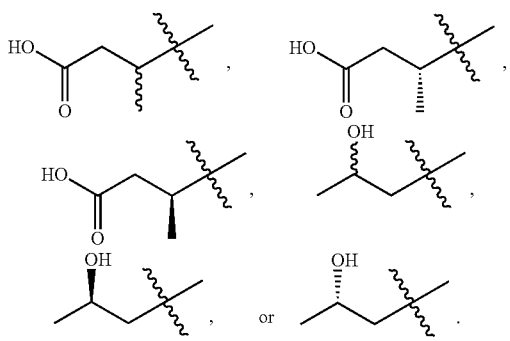

In an aspect, the present technology also provides compositions that include any embodiment of a compound of the present technology as disclosed herein and a pharmaceutically acceptable carrier.

In a related aspect, the present technology provides pharmaceutical compositions that include an effective amount of any embodiment of the compounds disclosed herein (or a pharmaceutically acceptable salt and/or solvate of any thereof) and a pharmaceutically acceptable carrier, wherein the effective amount is effective for increasing cellular respiration in a subject, increasing glycolytic flux in a subject, and/or treating a subject suffering from a neurodegenerative disease (e.g., Alzheimer's disease), multiple sclerosis, and/or epilepsy.

Further aspects are directed to methods of use of a compound of the present technology, including methods of treatment by administration of a compound of the present technology.

BRIEF DESCRIPTION OF THE DRAWINGS

FIGS. 1A-1D provide that a 2-oxosuccinic acid (oxaloacetic acid or OAA) bioenergetic treatment increased cellular respiration by ~50%, similar to glucose restriction, and also increased glycolysis flux capacity by about 50%, according to the working examples. In particular, FIG. 1A provides the $NAD^+/NADH$ ratio upon addition of exogenous OAA; FIGS. 1B-1C illustrate the increased glycolysis rate (FIG. 1B) and increased respiration rate (FIG. 1C) provided by administering OAA in SH-SY5Y human neuroblastoma cells; and FIG. 1D provides an overall illustrative schematic of bioenergetic flux. **$p<0.01$. For the sake of clarity, for FIG. 1B the data is presented (going from left to right) as CON, 2 mM OAA, 2 mM MA, and 2 mM PYRUVATE; for FIG. 1C, the data is presented (going from left to right) as CON. OAA, MALATE, GLUCOSE DEPRIVATION, and PYRUVATE.

FIG. 3A provides the oxygen consumption rate (OCR; indicative of cellular respiration) over time of SH-SY5Y neuroblastoma cells after the addition of differing concentrations OAA(PG)$_2$ in comparison to a control as well as to background values, and FIG. 3B charts the effect that OAA(PG)$_2$ concentrations have on glycolysis in SH-SY5Y neuroblastoma cells, evidencing that OAA(PG)$_2$ concentrations that enhance respiration have an insignificant effect on glycolysis. ECAR=extracellular acidification rate. For the sake of clarity, for FIG. 3B the data are presented (going from left to right) as Control, 1 mM OAA(PG)$_2$, 2 mM OAA(PG)$_2$, and 5 mM OAA(PG)$_2$.

FIG. 5A shows ketone levels before and 45 min after administration of OAA(D-BHB)$_2$ on the first and second days of the experiment according to the present examples. FIG. 5B shows ketone level fold-change as a function of that day's baseline.

FIG. 6A is a bar graph showing the body weight average over the course of 5 days in treated mice vs. controls, according to the present examples. FIG. 6B shows a line graph showing the body weight average over the course of 5 days in treated mice vs. controls.

FIG. 7 shows the effects of the disodium salt of OAA(D-BHB)$_2$ (referred to as "OAA-D-BHB" in FIG. 7) or the disodium salt of racemic OAA(BHB)$_2$ (referred to as "OAA-D/L-BHB" in FIG. 7) on cellular respiration.

DETAILED DESCRIPTION

Figure 1A:
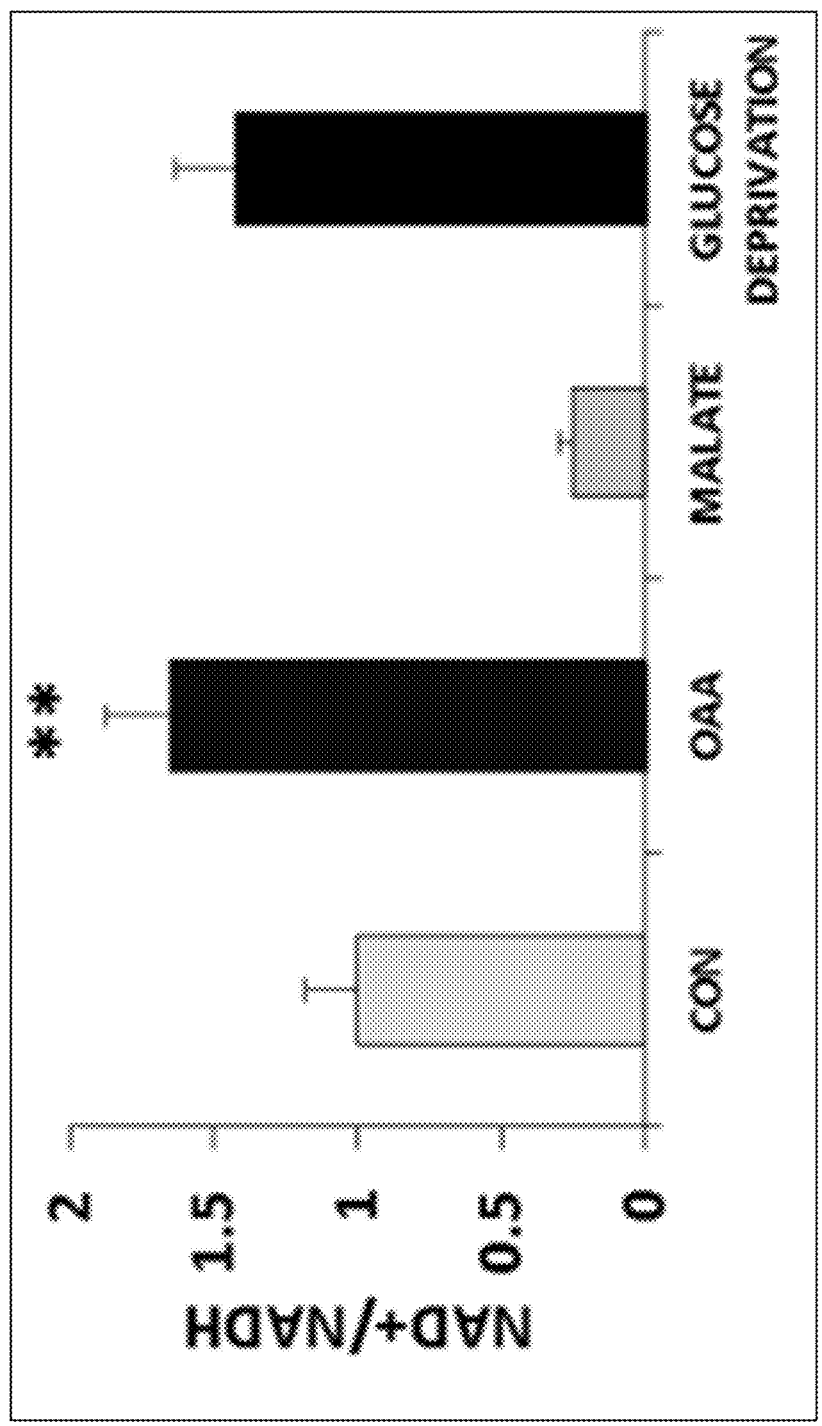

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term—for example, "about 10 wt. %" would be understood to mean "9 wt. % to 11 wt. %." It is to be understood that when "about" precedes a term, the term is to be construed as disclosing "about" the term as well as the term without modification by "about"—for example, "about 10 wt. %" discloses "9 wt. % to 11 wt. %" as well as disclosing "10 wt. %."

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

Pharmaceutically acceptable salts of compounds described herein are within the scope of the present technology and include acid or base addition salts which retain the desired pharmacological activity and is not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g. alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, or a hydroxyl group(s) it can form salts with metals, such as alkali and earth alkali metals (e.g. $Na^+$, $K^+$, $Ca^{2+}$, $Mg^{2+}$, $Zn^{2+}$)ammonia or organic amines (e.g. dicyclohexylamine, trimethylamine, triethylamine, pyridine, picoline, ethanolamine, diethanolamine, triethanolamine) or basic amino acids (e.g. arginine, lysine and ornithine). Such salts can be prepared in situ during isolation and purification of the compounds or by separately reacting the purified compound in its free base or free acid form with a suitable acid or base, respectively, and isolating the salt thus formed.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as mixtures of these various different forms. The phrase "and/or" as used in this paragraph and the present disclosure will be understood to mean any one of the recited members individually or a combination of any two or more thereof—for example, "A, B, and/or C" would mean "A, B, C, A and B, A and C, or B and C."

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, quinazolinones may exhibit the following isomeric forms, which are referred to as tautomers of each other:

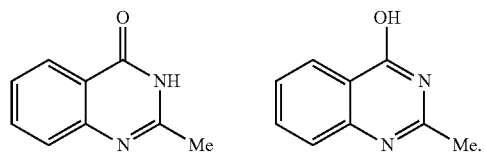 [SMILES: Cc1nc2ccccc2c(=O)[nH]1 ; Cc1nc(O)c2ccccc2n1]

As another example, guanidines may exhibit the following isomeric forms in protic organic solution, also referred to as tautomers of each other:

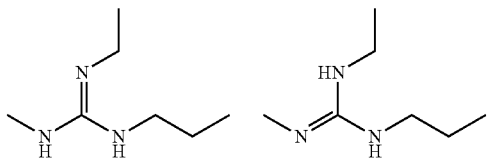

Because of the limits of representing compounds by structural formulas, it is to be understood that all chemical formulas of the compounds described herein represent all tautomeric forms of compounds and are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

The compounds of the present technology may exist as solvates, especially hydrates. Hydrates may form during manufacture of the compounds or compositions comprising the compounds, or hydrates may form over time due to the hygroscopic nature of the compounds. Compounds of the present technology may exist as organic solvates as well, including DMF, ether, and alcohol solvates among others. The identification and preparation of any particular solvate is within the skill of the ordinary artisan of synthetic organic or medicinal chemistry.

"Cellular respiration," used herein, is a set of metabolic reactions and processes that take place in the cells of organisms to convert biochemical energy from nutrients into adenosine triphosphate (ATP), and then release waste products. Increases or decreases in cellular respiration may be measured as described in the Examples, such as by measuring oxygen consumption rate (OCR).

"Glycolytic flux" refers to the rate at which molecules proceed through the glycolytic pathway or glycolysis in a cell.

As used herein, the terms "subject," "individual," or "patient" can be an individual organism, a vertebrate, a mammal, or a human. "Mammal" includes a human, non-human primate, murine (e.g., mouse, rat, guinea pig, hamster), ovine, bovine, ruminant, lagomorph, porcine, caprine, equine, canine, feline, avis, etc. In any embodiment herein, the mammal is feline or canine. In any embodiment herein, the mammal is human.

The term "administering" a compound or composition to a subject means delivering the compound to the subject. "Administering" includes prophylactic administration of the compound or composition (i.e., before the disease and/or one or more symptoms of the disease are detectable) and/or therapeutic administration of the composition (i.e., after the disease and/or one or more symptoms of the disease are detectable). The methods of the present technology include administering one or more compounds or agents. If more than one compound is to be administered, the compounds may be administered together at substantially the same time, and/or administered at different times in any order. Also, the compounds of the present technology may be administered before, concomitantly with, and/or after administration of another type of drug or therapeutic procedure (e.g., surgery).

As used herein, the terms "effective amount" or "therapeutically effective amount," or "pharmaceutically effective amount" refer to a quantity sufficient to achieve a desired therapeutic and/or prophylactic effect, e.g., an amount which results in the full or partial amelioration of disease or disorders or symptoms associated with mitochondrial dysfunction, neurological disease, lack of energy, glycolytic process dysfunction or cellular respiration related dysfunction in a subject in need thereof. In the context of therapeutic or prophylactic applications, the amount of a composition administered to the subject will depend on the type and severity of the disease and on the characteristics of the individual, such as general health, age, sex, body weight and tolerance to drugs. It will also depend on the degree, severity and type of disease. A person of ordinary skill in the art will be able to determine appropriate dosages depending on these and other factors. The compositions can also be administered in combination with one or more additional compounds. Multiple doses may be administered. Additionally or alternatively, multiple therapeutic compositions or compounds may administered. In the methods described herein, the compounds may be administered to a subject having one or more signs or symptoms of a disease or disorder described herein.

"Treating," "treat," "treated," or "treatment" as used herein covers the treatment of a disease or disorder described herein (e.g., AD), in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, ameliorating, or slowing progression of one or more symptoms of the disease or disorder. Symptoms may be assessed by methods known in the art or described herein, for example, biopsy, histology, and blood tests to determine relevant enzyme levels, metabolites or circulating antigen or antibody (or other biomarkers), quality of life questionnaires, patient-reported symptom scores, and imaging tests.

"Ameliorate," "ameliorating," and the like, as used herein, refer to inhibiting, relieving, eliminating, or slowing progression of one or more symptoms.

As used herein, "prevention," "prevents," or "preventing" of a disorder or condition refers to a compound that, in a statistical sample, reduces the occurrence of the disorder, symptom, or condition in the treated sample relative to a control subject, or delays the onset of one or more symptoms of the disorder or condition relative to the control subject.

Throughout this disclosure, various publications, patents and published patent specifications are referenced by an identifying citation. Also within this disclosure are Arabic numerals referring to referenced citations, the full bibliographic details of which are provided subsequent to the Examples section. The disclosures of these publications, patents and published patent specifications are hereby incorporated by reference into the present disclosure to more fully describe the present technology.

The Present Technology

Bioenergetic dysfunction occurs in Alzheimer's disease (AD). While it is unclear at the present time whether bioenergetic dysfunction represents a primary or secondary pathology, targeting bioenergetic dysfunction provides for treatment of AD. While prior attempts at therapeutics for AD generally focus on sequelae of mitochondrial dysfunction or energy failure (such as oxidative stress), specific pharmacologic strategies designed to manipulate bioenergetic fluxes remain relatively untested.

The compound oxaloacetate (OAA) can concomitantly enhance both glycolysis and respiration fluxes, where a study performed in mice illustrated OAA activates brain mitochondrial biogenesis-promoting proteins, enhances activity of the brain insulin signaling pathway, reduces neuroinflammation-related activity, and increases hippocampal neurogenesis. See Wilkins H. M., et al. Oxaloacetate activates brain mitochondrial biogenesis, enhances the insulin pathway, reduces inflammation, and stimulates neurogenesis. Hum Mol Genet 2014; 23:6528-6541. However, a Phase 1B clinical trial of OAA in AD patients (Swerdlow, clinicaltrials.gov NCT02593318) found limited quantifiable changes in plasma OAA after daily oral dosing. Moreover, OAA is unstable in solution and poorly bioavailable, including decomposing via decarboxylation.

The present technology provides compounds, methods, and compositions useful in promoting bioenergetics processes and treating neurodegenerative diseases, including Alzheimer's disease (AD). The present technology provides compounds that include an OAA core esterified with particular motifs, where the compounds of the present technology are significantly more stable than OAA ex vivo as well as significantly more stable in vivo. While esterification of a carboxylic acid in general might appear a simple endeavor, due to the fugacious nature of OAA in myriad environments and in particular upon attempting multiple different esterification conditions and protocols (as discussed in additional further detail herein), a person of ordinary skill in the art would understand merely esterification of OAA is highly unpredictable, relies on random trial and error, and has not been accomplished for a variety of potential ester groups. Furthermore, person of ordinary skill in the art in view of known problems accompanying OAA and known OAA esters (e.g., oxaloacetic acid 4-methyl ester; diethyl oxaloacetate)—especially in attempting to administer to biological systems—would not possess any reliable guidance as to the stability and/or biological properties of an individual OAA ester absent experiments with the individual ester. The present technology is a significant advancement independently and further significantly supports bioenergetic metabolism.

The present technology provides a further significant advance, especially in regard to treating neurodegenerative conditions, multiple sclerosis, and/or epilepsy. The examples and data herein evidence that use of the compounds of the present technology in biological systems significantly increases cellular respiration and glycolytic flux, especially as compared to OAA, and thus significantly supports bioenergetics metabolism.

Thus, in an aspect of the present technology, a compound of Formula I is provided

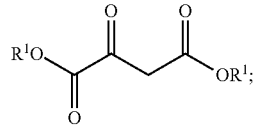
(I)

or a pharmaceutically acceptable salt and/or solvate thereof, wherein both $R^1$ are selected from:

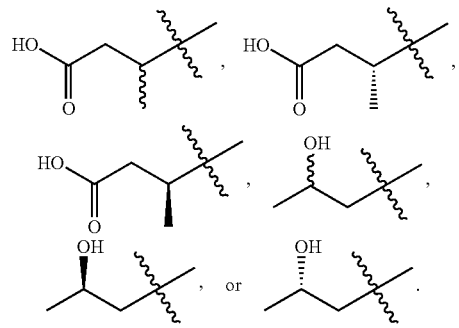

In any embodiment disclosed herein, the compound of Formula I may be

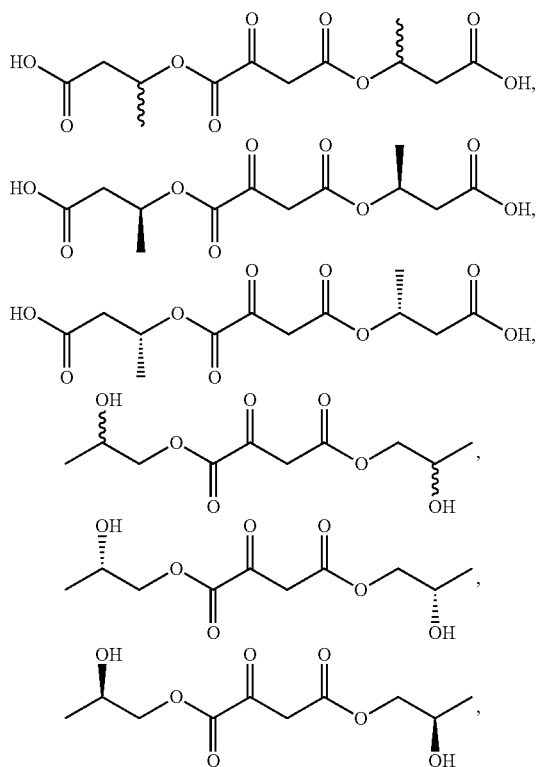

or a pharmaceutically acceptable salt and/or solvate thereof of any one of these. In any embodiment disclosed herein, the compound of Formula I may be a sodium salt of

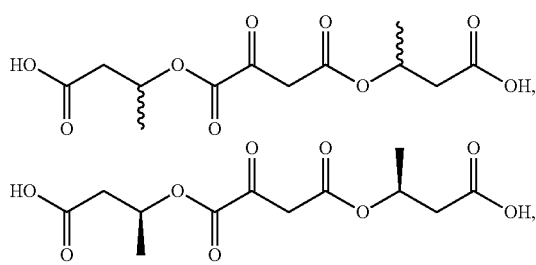

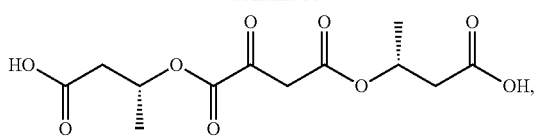

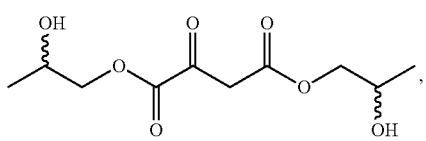

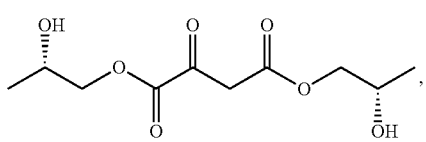

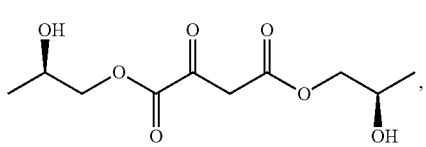

or a solvate thereof of any one of these. In any embodiment disclosed herein, the compound of Formula I may be a potassium salt of

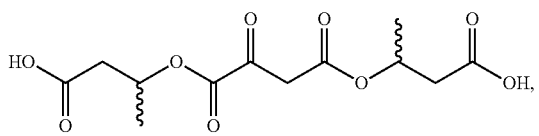

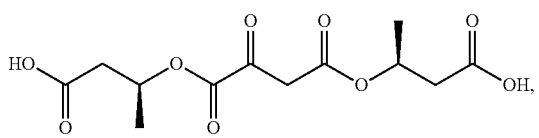 [SMILES: C[C@@H](CC(=O)O)OC(=O)CC(=O)C(=O)O[C@@H](C)CC(=O)O]

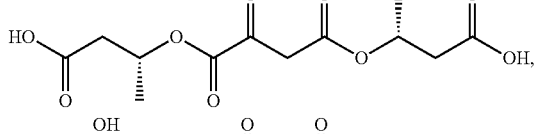

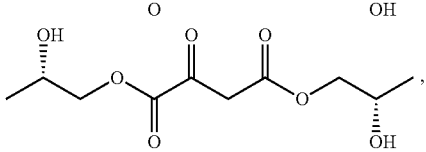

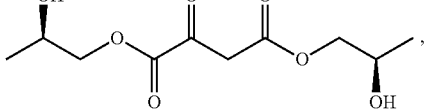

or a solvate thereof of any one of these. For example, the compound of Formula I may be a potassium salt of

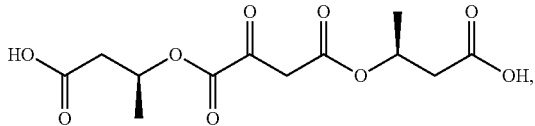 [SMILES: C[C@@H](CC(=O)O)OC(=O)CC(=O)C(=O)O[C@@H](C)CC(=O)O]

a dipotassium salt of

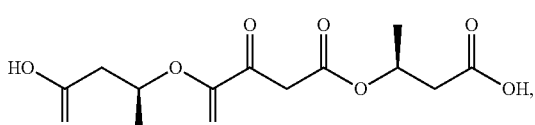

a sodium salt of

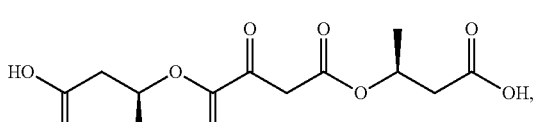

a disodium salt of

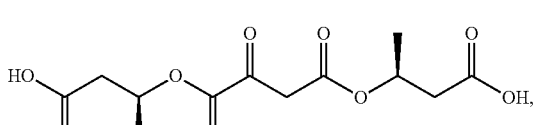

a sodium potassium salt of

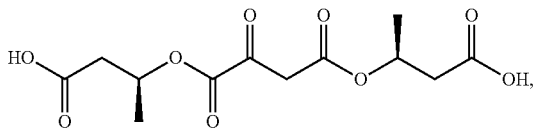 [SMILES: C[C@@H](CC(=O)O)OC(=O)CC(=O)C(=O)O[C@@H](C)CC(=O)O]

or a solvate thereof of any one of these.

In a related aspect, a composition is provided that includes a compound of Formula I of any embodiment disclosed herein (e.g., a compound according to Formula I, a compound disclosed above, a pharmaceutically acceptable salt and/or solvate of any compound disclosed above) and a pharmaceutically acceptable carrier or one or more excipients, fillers or agents (collectively referred to hereafter as "pharmaceutically acceptable carrier" unless otherwise indicated and/or specified). In a related aspect, a medicament is provided that includes a compound of Formula I of any embodiment disclosed herein. In a related aspect, a pharmaceutical composition is provided that includes (i) an effective amount of a compound of Formula I of any embodiment disclosed herein, and (ii) a pharmaceutically acceptable carrier. For ease of reference, the compositions, medicaments, and pharmaceutical compositions of the present technology may collectively be referred to herein as "compositions." In further related aspects, the present technology provides methods including a compound of any embodiment disclosed herein and/or a composition of any embodiment disclosed herein as well as uses of a compound of any embodiment disclosed herein and/or a composition of any embodiment disclosed herein. Such methods and uses may include an effective amount of a compound of any embodiment disclosed herein. In any aspect or embodiment disclosed herein (collectively referred to herein as "any embodiment herein," "any embodiment disclosed herein," or the like), the effective amount may be an amount that increases cellular respiration and/or glycolytic flux in a subject. Such an increase may be an increase over cellular respiration and/or glycolytic flux absent administration of the compound; such an increase may be an increase over cellular respiration and/or glycolytic flux as compared to administration of an equivalent amount of OAA in terms of moles of OAA. In any embodiment herein, the effective amount may be an amount that treats a neurodegenerative disease in a subject. The neurodegenerative disease of any embodiment herein may include Alzheimer's disease, Parkinson's disease, and/or amyotrophic lateral sclerosis (also known as motor neuron disease as well as Lou Gehrig's disease). See, e.g., Nishimune H, Tungtur S, Wilkins H, Swerdlow R, Sage J, Agbas, B, Barohn R. Beneficial effect of oxaloacetate for the neuromuscular function of SOD1G93A mice. 28$^{th}$ International Symposium of the Motor Neurone Disease Association, 2017; Swerdlow R H, Lyons K E, Khosla S K, Nashatizadeh M, Pahwa R. A pilot Study of oxaloacetate 100 mg capsules in Parkinson's disease patients. JPA 2016; 3:4. In any embodiment herein, the effective amount may be an amount that treats multiple sclerosis in a subject. In any embodiment herein, the effective amount may be an amount that treats epilepsy in a subject. In any embodiment herein, the effective amount may be an amount that treats a mitochondrial disorder in a subject. In any embodiment herein, the effective amount may be an amount that improves athletic and/or cognitive performance in a subject. See, e.g., E L, Lu J, Selfridge J E, Burns J M, Swerdlow R H. Lactate administration reproduces specific brain and liver exercise-related changes. J Neurochem 2013; 127:91-100. Such an improvement may be a statistically significant over such performance absent administration of the compound; such an increase may be a statistically significant increase over such performance as compared to administration of an equivalent amount of OAA in terms of moles of OAA. In any embodiment herein, the effective amount may be an amount that increases ketone levels in a subject (including increasing ketone levels in blood and/or plasma of the subject by administering the compound; including increasing ketogenesis in the subject by administering the compound). By way of example, the effective amount of any embodiment herein may be from about 0.01 µg to about 200 mg of the compound per gram of the composition, and preferably from about 0.1 µg to about 10 mg of the compound per gram of the composition.

In any embodiment disclosed herein, the effective amount may be determined in relation to a subject. "Effective amount" refers to the amount of a compound or composition required to produce a desired effect. One non-limiting example of an effective amount includes amounts or dosages that yield acceptable toxicity and bioavailability levels for therapeutic (pharmaceutical) use including, but not limited to, the treatment of mitochondrial dysfunction, glycolytic dysfunction, a neurodegenerative disease (e.g., Alzheimer's disease, Parkinson's disease, and/or amyotrophic lateral sclerosis), multiple sclerosis, and/or epilepsy. Another example of an effective amount includes amounts or dosages that are capable of reducing or ameliorating symptoms associated with a neurodegenerative disease (e.g., Alzheimer's disease, Parkinson's disease, and/or amyotrophic lateral sclerosis). Non-limiting examples of symptoms associated with neurodegenerative disease include mental decline, difficulty thinking and understanding, confusion in the evening hours, delusion, disorientation, forgetfulness, making things up, mental confusion, difficulty concentrating, inability to create new memories, inability to do simple math, or inability to recognize common things, tremor, seizure, depression, hallucinations, paranoia, jumbled speech, lack of appetite, difficulty with movement, weakness, or any other symptom disclosed herein.

The pharmaceutical composition of any embodiment disclosed herein may be packaged in unit dosage form. The unit dosage form is effective in treating a neurodegenerative disease, bioenergetics dysfunction, glycolytic dysfunction, dysfunction in cellular respiration or to improve athletic and/or cognitive performance. Generally, a unit dosage including a compound of the present technology will vary depending on patient considerations. Such considerations include, for example, age, protocol, condition, sex, extent of disease, contraindications, concomitant therapies and the like. An exemplary unit dosage based on these considerations may also be adjusted or modified by a physician skilled in the art. For example, a unit dosage for a patient comprising a compound of the present technology may vary from $1\times10^{-4}$ g/kg to 1 g/kg, preferably, $1\times10^{-3}$ g/kg to 1.0 g/kg. Dosage of a compound of the present technology may also vary from 0.01 mg/kg to 100 mg/kg or, preferably, from 0.1 mg/kg to 10 mg/kg. Suitable unit dosage forms, include, but are not limited to parenteral solutions, oral solutions, powders, tablets, pills, gelcaps, capsules, lozenges, suppositories, patches, nasal sprays, injectables, implantable sustained-release formulations, mucoadherent films, topical varnishes, lipid complexes, liquids, etc.

The compositions of the present technology may be prepared by mixing one or more compounds of Formula I of any embodiment disclosed herein with one or more pharmaceutically acceptable carriers in order to provide a pharmaceutical composition useful to prevent and/or treat a neurodegenerative disease, prevent and/or treat a bioenergetics dysfunction, prevent and/or treat a glycolytic dysfunction, prevent and/or treat a dysfunction in cellular respiration, improve athletic performance, and/or improve cognitive performance. Such compositions may be in the form of, for example, granules, powders, tablets, capsules, syrup, suppositories, injections, emulsions, elixirs, suspensions or solutions. The instant compositions may be formulated for various routes of administration, for example, by oral, parenteral, topical, rectal, nasal, vaginal administration, or via implanted reservoir. Parenteral or systemic administration includes, but is not limited to, subcutaneous, intravenous, intraperitoneal, and intramuscular injections. The following dosage forms are given by way of example and should not be construed as limiting the present technology.

For oral, buccal, and sublingual administration, powders, suspensions, granules, tablets, pills, capsules, gel caps, and caplets are acceptable as solid dosage forms. These can be prepared, for example, by mixing one or more compounds of the instant present technology with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, enteric coatings, controlled release coatings, binders, thickeners, buffers, sweeteners, flavoring agents, perfuming agents, or a combination of any two or more thereof. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical compositions may be prepared as liquid suspensions or solutions using a sterile liquid, such as, but not limited to, an oil, water, an alcohol, and combinations of these. Pharmaceutically suitable surfactants, stabilizers, antioxidants, suspending agents, emulsifying agents, buffers, pH modifiers, or a combination of any two or more thereof, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as, but not limited to, poly(ethylene glycol), petroleum hydrocarbons such as mineral oil and petrolatum; and water may also be used in suspension formulations.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Additionally or alternatively, sterile oils may be employed as solvents or suspending agents. Typically, the oil or fatty acid is non-volatile, including natural or synthetic oils, fatty acids, mono-, di- or tri-glycerides.

For injection, the composition may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, buffers, surfactants, bioavailability modifiers, and combinations of any two or more of these.

Compounds of the present technology may be administered to the lungs by inhalation through the nose or mouth. Suitable compositions for inhalation include solutions, sprays, dry powders, or aerosols containing any appropriate solvents and optionally other compounds such as, but not limited to, stabilizers, antimicrobial agents, antioxidants, pH modifiers, surfactants, bioavailability modifiers and combinations of these. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aqueous and non-aqueous (e.g., in a fluorocarbon propellant) aerosols may be used for delivery of compounds of the present technology by inhalation.

Dosage forms for the topical (including buccal and sublingual) or transdermal administration of compounds of the present technology include powders, sprays, ointments, pastes, creams, lotions, gels, solutions, and patches. The active component may be mixed under sterile conditions with a pharmaceutically acceptable carrier and/or excipient, and with any preservatives, or buffers, which may be required. Powders and sprays can be prepared, for example, with excipients such as lactose, talc, silicic acid, aluminum hydroxide, calcium silicates and polyamide powder, or mixtures of these substances. The ointments, pastes, creams and gels may also contain excipients such as animal and vegetable fats, oils, waxes, paraffins, starch, tragacanth, cellulose derivatives, polyethylene glycols, silicones, bentonites, silicic acid, talc and zinc oxide, or mixtures thereof. Absorption enhancers can also be used to increase the flux of the compounds of the present technology across the skin. The rate of such flux can be controlled by either providing a rate controlling membrane (e.g., as part of a transdermal patch) or dispersing the compound in a polymer matrix or gel.

Besides those representative dosage forms described above, pharmaceutically acceptable excipients and carriers are generally known to those skilled in the art and are thus included in the instant present technology. Such excipients and carriers are described, for example, in "Remington's Pharmaceutical Sciences" Mack Pub. Co., New Jersey (1991), and "Handbook of Pharmaceutical Excipients" by Raymond Rowe. Pharmaceutical Press, London, UK (2009), each of which is incorporated herein by reference.

The compositions (e.g., pharmaceutical compositions) of the present technology may be designed to be short-acting, fast-releasing, long-acting, and sustained-releasing as described below. Thus, the compositions may also be formulated for controlled release or for slow release.

The compositions of the present technology may also include, for example, micelles or liposomes, or some other encapsulated form, or may be administered in an extended release form to provide a prolonged storage and/or delivery effect. Therefore, the compositions may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant present technology.

Various assays and model systems, for example those described herein, can be readily employed to determine the therapeutic effectiveness of the treatment according to the present technology.

For each of the indicated conditions described herein, test subjects will exhibit a 10%, 20%, 30%, 50% or greater reduction, up to a 75-90%, or 95% or greater, reduction, in one or more symptom(s) caused by, or associated with, the disorder in the subject, compared to placebo-treated or other suitable control subjects.

The present technology further provides a method of increasing cellular respiration in a cell, where the method includes contacting the cell with a compound of any of embodiment disclosed herein and/or with a composition of any embodiment disclosed herein. In any embodiment herein, the cell may be a neural cell, neuronal cell, glial cell, stem cell, a bone cell (for example, osteocytes, osteoblasts, or osteoclast), a blood cell (for example, erythrocyte or leukocyte), a muscle cell (for example, myocyte), a chondrocyte, a fat cell (for example, adipocyte), a skin cell (for example, epithelial cell), an endothelial cell, or a pancreatic cell. In any embodiment disclosed herein, the cell may be outside of a subject when performing the contacting step, such as in vitro and/or in a well in a well plate. The cell of any embodiment may be a mammalian cell, such as a mouse cell, a rat cell, or a human cell (e.g., a human neuronal cell).

The present technology also provides a method of increasing a ratio of cytosolic $NAD^+$ to NADH in a cell, where the method includes contacting the cell with a compound of any embodiment disclosed herein and/or contacting the cell with a composition of any embodiment disclosed herein. In any embodiment disclosed herein, the cell may be outside of a subject when performing the contacting step, such as in vitro and/or in a well in a well plate. The cell of any embodiment may be a mammalian cell, such as a mouse cell, a rat cell, or a human cell (e.g., a human neuronal cell).

In any embodiment herein, the cell may be a neural cell, neuronal cell, glial cell, stem cell, a bone cell (for example, osteocytes, osteoblasts, or osteoclast), a blood cell (for example, erythrocyte or leukocyte), a muscle cell (for example, myocyte), a chondrocyte, a fat cell (for example, adipocyte), a skin cell (for example, epithelial cell), an endothelial cell, or a pancreatic cell.

The present technology further provides a method of increasing glycolytic flux in a cell, where the method includes contacting the cell with a compound of any of embodiment disclosed herein and/or contacting the cell with a composition of any embodiment disclosed herein, or by contacting the cell with metabolites or hydrolyzed products that have resulted from the administration of a compound of any embodiment disclosed herein. In any embodiment disclosed herein, the cell may be outside of a subject when performing the contacting step, such as in vitro and/or in a well in a well plate. The cell of any embodiment may be a mammalian cell, such as a mouse cell, a rat cell, or a human cell (e.g., a human neuronal cell).

In any embodiment herein, the cell may be a neural cell, neuronal cell, glial cell, stem cell, a bone cell (for example, osteocytes, osteoblasts, or osteoclast), a blood cell (for example, erythrocyte or leukocyte), a muscle cell (for example, myocyte), a chondrocyte, a fat cell (for example, adipocyte), a skin cell (for example, epithelial cell), an endothelial cell, or a pancreatic cell.

In a related aspect, a method of treating a subject suffering from a neurodegenerative disease is provided, where the method includes administering to the subject an effective amount of a compound of any embodiment disclosed herein. The method may include administering to the subject a composition of any embodiment disclosed herein. The neurodegenerative disease may be Alzheimer's disease (AD), Parkinson's disease (PD), amyotrophic lateral sclerosis, or a combination of any two or more thereof.

In any embodiment disclosed herein, the method may ameliorate and/or prevent at least one symptom selected from (a) a symptom from the Integrated Alzheimer's Disease Rating Scale (iADRS) selected from the group consisting of personal belonging management, selection of clothes, ability to dress self, ability to clean habitation, financial management ability, writing ability, ability to keep appointments, ability to use telephone, ability to prepare food for self, travel ability, awareness of current events, reading ability, interest in television, ability to shop for self, ability to remain alone, ability to perform chores, ability to perform a hobby or game, driving ability, self-management of medications, ability to initiate and finish complex tasks, and ability to initiate and finish simple tasks; (b) a sign from the Alzheimer's Disease Assessment Scale-Cognitive subscale (ADAS-Cog) selected from the group consisting of learning, naming, command following, ideational praxis, constructional praxis, orientation, and recognition memory; (c) a symptom from the Alzheimer's Disease Cooperative Study—instrumental Activities of Daily Living (ADCS-iADL) wherein the symptom is any of the symptoms recited in (a) or (b); (d) constipation; (e) depression; (f) cognitive impairment; (g) short or long term memory impairment; (h) concentration impairment; (i) coordination impairment; (j) mobility impairment; (k) speech impairment; (l) mental confusion; (m) sleep problem, sleep disorder, or sleep disturbance; (n) circadian rhythm dysfunction; (o) REM disturbed sleep; (p) REM behavior disorder; (q) hallucinations; (r) fatigue; (s) apathy; (t) erectile dysfunction; (u) mood swings; (v) urinary incontinence; or (w) neurodegeneration.

Amelioration of a symptom is measured using a clinically recognized scale or tool. Further, the amelioration of the symptom may be, for example, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100%, as measured using a clinically recognized scale or test, for example, any of those described herein.

In the method treating a subject suffering from a neurodegenerative disease, a compound of any embodiment herein of the present technology may be administered in combination with at least one additional active agent. Such an additional active agent may be administered (a) concomitantly; (b) as an admixture; (c) separately and simultaneously or concurrently; or (d) separately and sequentially, with respect to the compound of the present technology. In any embodiment herein, the at least one additional active agent may be an active agent used to treat AD or a symptom thereof, e.g., cholinesterase inhibitors such as donepezil (Aricept®), galantamine (Razadyne®), rivastigmine (Exelon®), and tacrine (Cognex®); N-methyl D-aspartate (NMDA) antagonists such as memantine (Namenda®); and Namzaric®, a combination of Namenda® and Aricept®; or a combination of any two or more thereof.

In any embodiment disclosed herein, the subject may be at risk for developing, or is suffering from, neurodegeneration via the neurodegenerative disease, and the method results in treating, preventing, and/or delaying the progression and/or onset of neurodegeneration in the subject. The neurodegeneration may be associated with Alzheimer's disease, Parkinson's disease, amyotrophic lateral sclerosis, or a combination of any two or more thereof. For example, progression or onset of AD may be slowed, halted, or reversed over a defined time period following administration of a compound of the present technology, as measured by a medically-recognized technique; and/or the subject with AD may be positively impacted by administration of a compound of the present technology, as measured by a medically-recognized technique.

In any embodiment disclosed herein, amelioration of the symptom or treatment of AD is measured quantitatively or qualitatively by one or more techniques selected from the group consisting of electroencephalogram (EEG), neuroimaging, functional MRI, structural MRI, diffusion tensor imaging (DTI), [18F]fluorodeoxyglucose (FDG) PET, agents that label amyloid, [18F]F-dopa PET, radiotracer imaging, volumetric analysis of regional tissue loss, specific imaging markers of abnormal protein deposition, multimodal imaging, and biomarker analysis. In any embodiment disclosed herein, progression or onset of AD is slowed, halted, or reversed by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, as measured by a medically-recognized technique, via administration of a compound of the present technology.

In a related aspect, a method of improving cognitive and/or athletic performance in a subject is provided, where the method includes administering an effective amount of a compound of any embodiment disclosed herein to the subject. In any embodiment herein, the method may further include administering one or more additional agents selected from caffeine, ginseng, vitamin B6, vitamin B12, niacin, folic acid, taurine, green tea extract, theanine, guarana extract, Ginkgo biloba, or carnitine. In any embodiment herein, the method may include administering a composition of any embodiment disclosed herein where the composition further includes the one or more additional agents. Improvements in cognitive performance may measured qualitatively or quantitatively by any method known to a person of ordinary skill in the art, non-limiting examples include ADASCog, Mini-Mental State Exam (MMSE), Mini-cog test, Woodcock-Johnson Tests of Cognitive Abilities, Leiter International Performance Scale, Miller Analogies Test, Raven's Progressive Matrices, Wonderlic Personnel Test, IQ tests, or a computerized tested selected from Cantab Mobile, Cognigram, Cognivue, Cognision, or Automated Neuropsychological Assessment Metrics Cognitive Performance Test (CPT). Improvements in athletic performance may be measured quantitatively or qualitatively by any method known to a person of ordinary skill in the art. Non-limiting examples include measurement of running speed, jumping height, endurance, distance and object is thrown, or weight lifted. In any embodiment herein, cognitive and/or athletic performance may be improved by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, as measured by any of the above measurement techniques.

In any embodiment herein, administration may include but not be limited to, parenteral, intravenous, intramuscular, intradermal, intraperitoneal, intratracheal, subcutaneous, oral, intranasal/respiratory (e.g., inhalation), transdermal (topical), sublingual, ocular, vaginal, rectal, or transmucosal administration.

In any embodiment herein the compound may be administered daily for an extended period of time. Periods of time include 1-4 weeks, 1-3 months, 1-6 months, one month to a year, or for more than one year. In any embodiment herein, the compound may be administered for the lifetime of the subject. The amount of compound administered daily may be fixed, increase daily, weekly, monthly or yearly. In any embodiment herein, the administration is once, twice, thrice or four or greater times a day. In an embodiment of any method disclosed herein, administering a compound of any embodiment herein comprises administering a pharmaceutical composition disclosed herein.

In any embodiment herein, the effective amount may be precisely, at least, above, up to, or less than, 1 mg, 10 mg, 50 mg, 100 mg, 200 mg, 300 mg, 400 mg, 500 mg, 600 mg, 700 mg, 800 mg, 900 mg, 1,000 mg, 1,200 mg, 1,500 mg, 2,000 mg, 2,500 mg, 3,000 mg, 3,500 mg, 4,000 mg, 4,500 mg, 5,000 mg, 5,500 mg, 6,000 mg, 6,500 mg, 7,000 mg, or any range including and/or in between any two of these values.

In any embodiment herein, the subject may be a mammal, such as a human, non-human primate, a murine (e.g., mouse, rat, guinea pig, hamster), an ovine, a bovine, a ruminant, a lagomorph, a porcine, a caprine, an equine, a canine, a feline, etc. In any embodiment herein, the subject may be a human.

EXAMPLES

The examples herein are provided to illustrate advantages of the present technology and to further assist a person of ordinary skill in the art with preparing and/or using the compounds of the present technology. The examples herein are also presented in order to more fully illustrate the preferred aspects of the present technology. The examples should in no way be construed as limiting the scope of the present technology. The examples can include or incorporate any of the variations, aspects, or embodiments of the present technology described above. The variations, aspects, or embodiments described above may also further each include or incorporate the variations of any or all other variations, aspects or embodiments of the present technology.

Example 1: Synthesis of Compounds of the Present Technology

The non-trivial esterification of OAA: Synthesis of OAA esters are difficult due to the chemical nature of OAA. For example, OAA is prone to decarboxylation; when esterified, OAA is prone to form an enolate under basic conditions; and esters of OAA tend to be readily hydrolyzed. See, e.g., Tsai, C. S. Spontaneous decarboxylation of oxalacetic acid. Canadian Journal of Chemistry, 1967, Vol. 45, 873-880; Sucrow, W, Grosz, K-P. A Convenient Preparation of Dimethyl and Diethyl Oxaloacetate. Synthetic Communication, 1979, Vol. 9(7), 603-607; Hatch, M. D., Heldt, H. W. Synthesis, Storage, and Stability of [4-$^{14}$C]-Oxaloacetic Acid Analytic Biochemistry, 1985, Vol. 145, 393-397; U.S. Pat. Publ. 2016/0235696. Myriad differing strategies for synthesizing esters of OAA were designed and performed but did not result in successful esterification. For example, in approaches utilizing a diacyl chloride of OAA, multiple different bases were utilized such as DIEA, pyridine, and KOtBu, where all efforts these failed to produce the desired esterified OAA. DMAP was also used as a catalyst but also did not result in success. Other failed routes include the use of DCC and EDC with catalytic amounts of DMAP as well as ester formation via lipase.

After numerous different attempts and strategies, the only synthetic procedure that resulted in success included using the diacyl chloride of OAA as well as preincubating BHB or PG with NaH prior to reaction with the diacyl chloride of OAA (discussed in detail below). Furthermore, this procedure provided minimal side products.

General Procedure for the Synthesis of OAA(BHB)$_2$ and OAA(PG)$_2$: OAA (1 equivalent) was dissolved in anhydrous dichloromethane (DCM) (0.1 M based off OAA) with a catalytic amount of dimethylformamide (DMF) (~1 drop). Oxalyl chloride (2.5 equivalents) was added dropwise and the reaction was stirred at room temperature for 2 hours. The vial was evaporated to dryness to yield a yellow oil containing the diacyl chloride of OAA. In a separate vial, 2 equivalents of the appropriate alcohol (3-hydroxybutanoic acid if synthesizing OAA(BHB)$_2$ or propane-1,2-diol if synthesizing OAA(PG)$_2$) and NaH (2 equivalents) were suspended in DCM and stirred for 30 minutes. The diacyl chloride of OAA was redissolved in DCM and DMF and added dropwise to the vial containing the alcohol and NaH. The reaction was left to stir overnight, after which the solvent was evaporated to obtain the product.

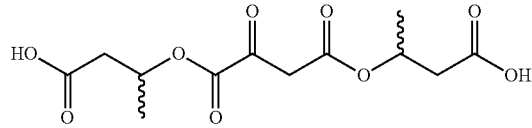

1

OAA(BHB)$_2$ (also referred to as compound 1): 3,3'-((2-oxosuccinyl)bis(oxy))dibutyric acid was synthesized according to the general procedure above to obtain an orange oil 1 in 59% yield. $^1$H NMR (400 MHz, Chloroform-d) δ 5.37 (m, 2H), 3.74 (s, 2H), 3.22 (m, 4H), 2.68 (m, 4H), 1.36 (m, 6H). HRMS (m/z): [M−H] calc'd for $C_{12}H_{15}O_9$, 303.0716; found 303.0731 (4.9 ppm).

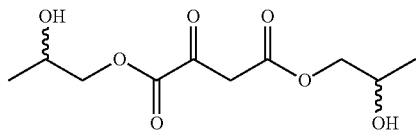 [SMILES: CC(O)COC(=O)CC(=O)C(=O)OCC(C)O]

2

OAA(PG)$_2$ (also referred to as compound 2): Bis(2-hydroxypropyl) 2-oxosuccinate was synthesized according to the general procedure above to obtain an orange oil 2 in 71% yield. $^1$H NMR (400 MHz, Chloroform-d) δ 5.23 (s, 2H), 4.5-3.9 (m, 8H), 1.35 (d, J=7.44 Hz, 6H). HRMS (m/z): [M+H] calc'd for $C_{10}H_{15}O_7$, 247.0818; found 247.0820 (0.8 ppm).

Similar procedures as described above were also utilized to generate OAA mono-ester with 3-hydroxybutanoic acid (also referred to herein as "OAA(BHB)(H)"; HRMS (m/z): [M−H]$^−$ calcd for $C_8H_9O_7$, 217.0348; found 217.0327 (9.7 ppm)) as well as the OAA mono-ester with propane-1,2-diol (also referred to herein as "OAA(PG)(H)").

Synthesis and of OAA-(BHB)$_2$ neutral form: In a particular batch, 2.00 g of oxalacetic acid (OAA) (15.1 mmol) was mixed with 3.00 mL dimethylformamide (DMF) (38.7 mmol, 2.6 equiv) and 3.30 mL oxalyl chloride (38.5 mmol, 2.5 equiv) for 3 h at 0° C. in 200 mL anhydrous dichloromethane (DCM), yielding a clear yellow solution. After 3 h, the reaction was then combined with a reaction that contained 3.83 g b-hydroxy butyric acid sodium salt (R-BHB-Na) (30.4 mmol, 2.01 equiv) that was reacted with 760 mg NaH (32.00 mmol, 2.1 equiv) for 2 h, which was also carried out in 200 mL anhydrous DCM at 0° C. The combined reactions were left to stir and warm to room temperature (ca. 20° C.) overnight and concentrated in vacuo to afford an orange-red oil, the neutral acid, with a yield of ca. 70%

The salts were prepared by taking the above product in DCM and extracting and neutralizing with a solution of bicarbonate. As a specific example, the disodium salt of a batch of OAA-(BHB)$_2$ was prepared by calculating the amount of NaHCO$_3$ necessary to fully deprotonate OAA-(BHB)$_2$ based on the theoretical yield of the reaction, then adding an additional 750 mg to that amount (ca. 3.25 g NaHCO$_3$ total for a 2 g scale reaction on an OAA basis), and dissolving the bicarbonate salt in 150 mL water. The oily residue was resuspended in 200 mL DCM, then the product was extracted into the aqueous phase beginning first with 100 mL of the NaHCO$_3$ solution, then adding small aliquots until the desired pH of 7 was reached. The red solution was then flash frozen in liquid nitrogen to form small spherical beads, followed by lyophilization over 2 days to afford the red hygroscopic solid OAA-(BHB Na)$_2$. Repeating the above procedure with an additional sample of the mother DCM liquor, but instead using potassium carbonate, yielded a red hygroscopic OAA(BHB K)$_2$ salt after lyophilization.

Purification of OAA-(BHB-Na)$_2$ using strong anion exchange chromatography: The product was purified using Dowex-1 strong-anion exchange resin. The material was adsorbed to the resin after deprotonation with aqueous sodium bicarbonate. By gradient elution using a CombiFlash Rf flash chromatography system (Teledyne ISCO, Lincoln, NE, USA), the disodium salt of OAA-(BHB)$_2$ was flushed off the resin using a water/1M NaCl solution binary solvent system. The column was flushed with 100% water for 5 column units, before increasing the 1M NaCl solution concentration from 0% to 100% over 10 column units. After holding at this concentration for another 5 column units, solvent system was returned to 100% water for cleaning. Most of the product was eluted at the 1M NaCl concentration, with a purity >95% by $^1$H NMR. This method was also employed using 1M sodium acetate and 1M sodium nitrate solutions with the same gradient method, affording lesser yields.

Example 2: In Vitro Testing of Bioenergetics Prodrugs OAA(BHB)$_2$ and OAA(PG)$_2$ Fluorodeoxyglucose positron emission tomography (FDG PET) and mitochondria studies demonstrate perturbed AD energy metabolism. FDG PET reveals focal reductions in brain glucose utilization with advancing age, which extend in magnitude and distribution during AD. Asymptomatic individuals with an APOE4 allele or AD-affected mother, who have an increased AD risk, show AD-like glucose utilization patterns. Neuron loss, synaptic degradation, or bona fide bioenergetic changes could contribute to reduced AD brain glucose utilization, although changes in pre- or asymptomatic subjects suggest the presence of true bioenergetic changes. AD subject brain homogenates also show less glucose consumption than control homogenates, even though homogenization disrupts synapses and neutralizes the impact of a synaptic loss component.

O$_2$ PET and homogenate studies show altered AD brain oxygen consumption, which likely reflects altered mitochondrial capacity or integrity. Electron microscopy reveals perturbed mitochondrial structures and mitochondrial fission increases. Several mitochondria-localized enzymes, including pyruvate dehydrogenase complex, α-ketoglutarate dehydrogenase complex, and cytochrome oxidase (COX) demonstrate reduced activities. The AD COX defect, interestingly, also exists outside the brain and at least partly depends on mitochondrial DNA (mtDNA). MtDNA alterations include reduced PCR-amplifiable levels despite an apparent increase in autophagosome-deposited mtDNA increased oxidative modifications, increased deletions, and possibly increased somatic point mutations.[1-3] Inherited mtDNA signatures reportedly associate with and influence AD risk, while epidemiologic and biomarker-based endophenotype studies show maternal inheritance bias. Apolipoprotein E4-derived peptides, amyloid precursor protein (APP), and Aβ co-localize with mitochondria and can disrupt their function. Alterations in tissues that do not accumulate Aβ, as well as the mtDNA-transferability of many alterations, though indicate Aβ is not the sole cause. Mitochondrial function and cell bioenergetics also influence APP processing.

The present technology provides a "bioenergetic medicine" approach to targeting AD energy metabolism dysfunction, as illustrated by the results of the present Example using representative compounds of the present technology. Bioenergetic medicine refers to the manipulation of bioenergetic fluxes to benefit health, such as improving cellular respiration and glycolysis.

Regarding diet, a ketogenic diet (KD) pilot study that found after 3 months on a KD, AD participant ADASCog scores improved by 4.1 points. KDs increase fat and reduce carbohydrate consumption.[4] This reduces insulin, which stimulates liver oxidation of fatty acids to ketone bodies (BHB, acetoacetate, and acetone) that enter the blood. Ventilation limits the more volatile acetone, while BHB and acetoacetate accumulate, access the brain, and fuel respiration. Given a choice between ketone bodies and glucose, neurons preferentially consume ketone bodies. Potentially related clinical studies include a caloric restriction (CR) trial that found CR improved memory in healthy adults. Ketone body production was not assessed, but CR does induce ketosis. Two studies report simply consuming a medium chain triglyceride (MCT) outside of a KD context, which also boosts serum BHB levels, at least temporarily improved cognition in AD subjects. See Henderson, S. T. et al. Study of the ketogenic agent AC-1202 in mild to moderate Alzheimer's disease: a randomized, double-blind, placebo-controlled, multicenter trial. Nutr Metab (Lond) 2009; 6:31; Reger, M. A. et al. Effects of beta-hydroxybutyrate on cognition in memory-impaired adults. Neurobiol Aging 2004; 25:311-314. Also, an exploratory human clinical study randomized 23 subjects with mild cognitive impairment (MCI), a frequent AD-precursor state, to a 6-week KD or high carbohydrate diet. Memory test performance improved in the KD (n=11) but not the high carbohydrate intervention. See Krikorian, R. et al. Dietary ketosis enhances memory in mild cognitive impairment. Neurobiol Aging 2012; 33:425 e419-427.

Animal studies reveal exercise affects the brain, and in particular enhances hippocampal neurogenesis. See, e.g., Greg Kennedy, G. et al. How Does Exercise Reduce the Rate of Age-Associated Cognitive Decline? A Review of Potential Mechanisms. JAD 55 (2017) 1-18. A variety of factors may mediate these effects, including muscle-generated lactate that enters the blood and accesses the brain. Lactate represents an important mitochondrial respiratory chain fuel source, particularly in neurons, and appears to play a critical role in memory formation. In terms of novel pharmacologic approaches, the study of Wilkins et al. concerned OAA administered to mice.[5] The primary rationale for evaluating OAA's effects on energy metabolism is that the cytosolic reduction of OAA to malate by the cytosolic malate dehydrogenase should increase NAD$^+$/NADH ratios, and thereby increase at least glycolytic flux. OAA administered by intraperitoneal (IP) injection promoted mitochondrial biogenesis parameters, enhanced insulin pathway signaling, lessened activity of the neuroinflammation-mediating NFκB transcription factor, and increased hippocampal neurogenesis. In this context, it is relevant to note AD brains exhibit decreased mitochondrial biogenesis, reduced insulin pathway signaling, NFκB activation with increased neuroinflammation, and perturbed hippocampal neurogenesis. The Wilkins et al. data was used to justify a PK study of a low OAA dose (100 mg BID) in AD participants, which did not reveal a reliable plasma level increase, and an AD clinical study using higher doses of up to 1 gram BID (Alzheimer's Association PCTR-15-330495; FDA IND125788). The Alzheimer's Association-supported study notes an excellent safety profile for OAA.

Results: The present technology provides safe and biostable compounds that concurrently enhance bioenergetic fluxes and cell energy production through multiple mechanisms.

Figure 1B:
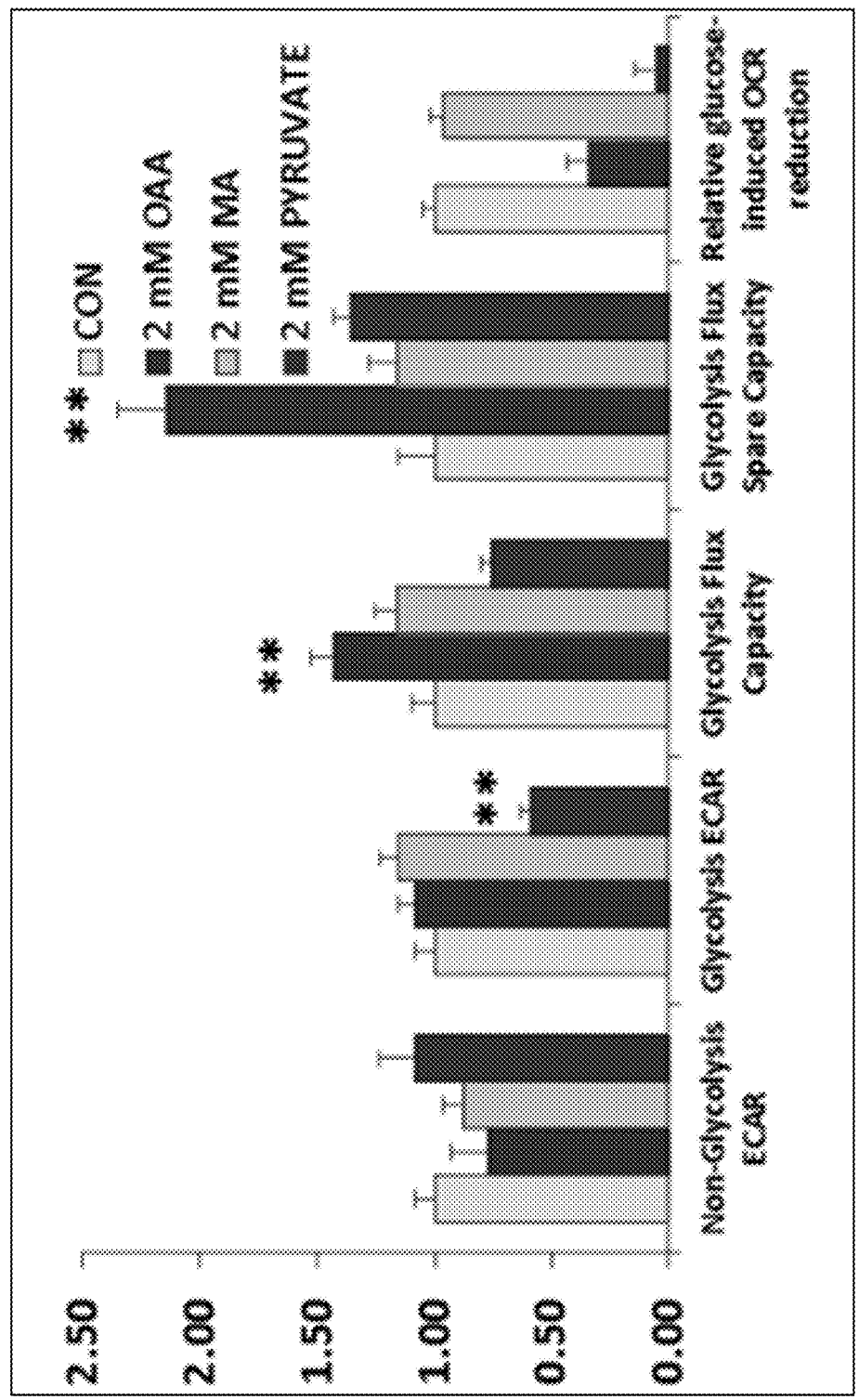
Figure 1D:
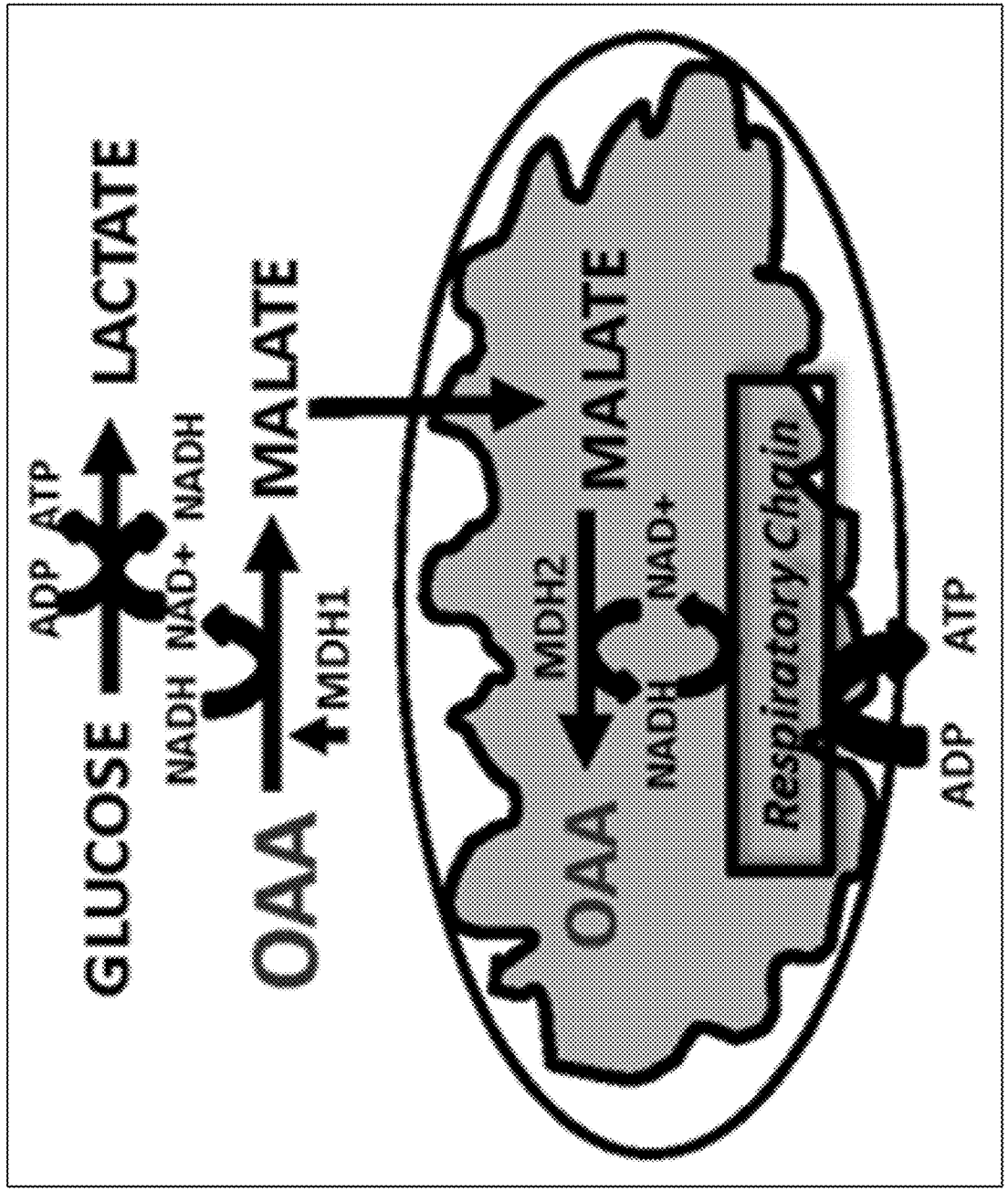

In regard to OAA, exogenously supplied OAA accesses the cell cytosol, where its reduction to malate converts NADH to NAD$^+$ (FIG. 1A). In FIG. 1A, SH-SY5Y cells were subjected to OAA, malate, glucose deprivation, or none of the above conditions, and NAD+ and NADH levels were measured in the cells to determine NAD+/NADH ratios. Glycolysis and respiratory fluxes were determined using a Seahorse Extracellular Flux analyzer for SH-SY5Y cells exposed to OAA, malate, or pyruvate (FIGS. 1B-1C). In these experiments, oligomycin, FCCP, rotenone/antimycin, and 2-deoxyglucose were used to determine the proportion of oxygen that was consumed as part of the mitochondrial "leak" and "ATP production"; maximum and spare flux rates were also determined using standard established flux analysis protocols. Unlike pyruvate, the other major cytosolic molecule whose reduction converts NADH to NAD$^+$, OAA is not a downstream glycolysis intermediate and it enhances rather than impedes glycolysis flux (FIG. 1B). Malate produced in the cytosol accesses mitochondria, enters the Krebs cycle, oxidizes to OAA in a reaction that generates mitochondrial NADH, and increases respiration (FIG. 1C). FIG. 1D schematically summarizes this pathway. Furthermore, OAA is unstable in solution and especially so in the presence of amino acids, undergoing rapid decarboxylation (~1%/min) into pyruvate, which has limited its pharmaceutical development.

BHB independently fuels energy metabolism. It is relevant to note a recent pilot study found AD participant cognition improved after three months of a ketogenic diet, an intervention that produces BHB. PG, a food additive, is "generally recognized as safe" (GRAS) and cells convert it to pyruvate and lactate. Experiments have shown that lactate and pyruvate effectively promote respiration, although in a tumor-derived cell line pyruvate also decreases glycolysis flux (see FIG. 1B). This is likely a consequence of the fact that pyruvate represents a downstream metabolite of glycolysis, and causes an inhibitory effect on the upstream glycolysis enzyme phosphofructokinase (PFK).

Figure 2:
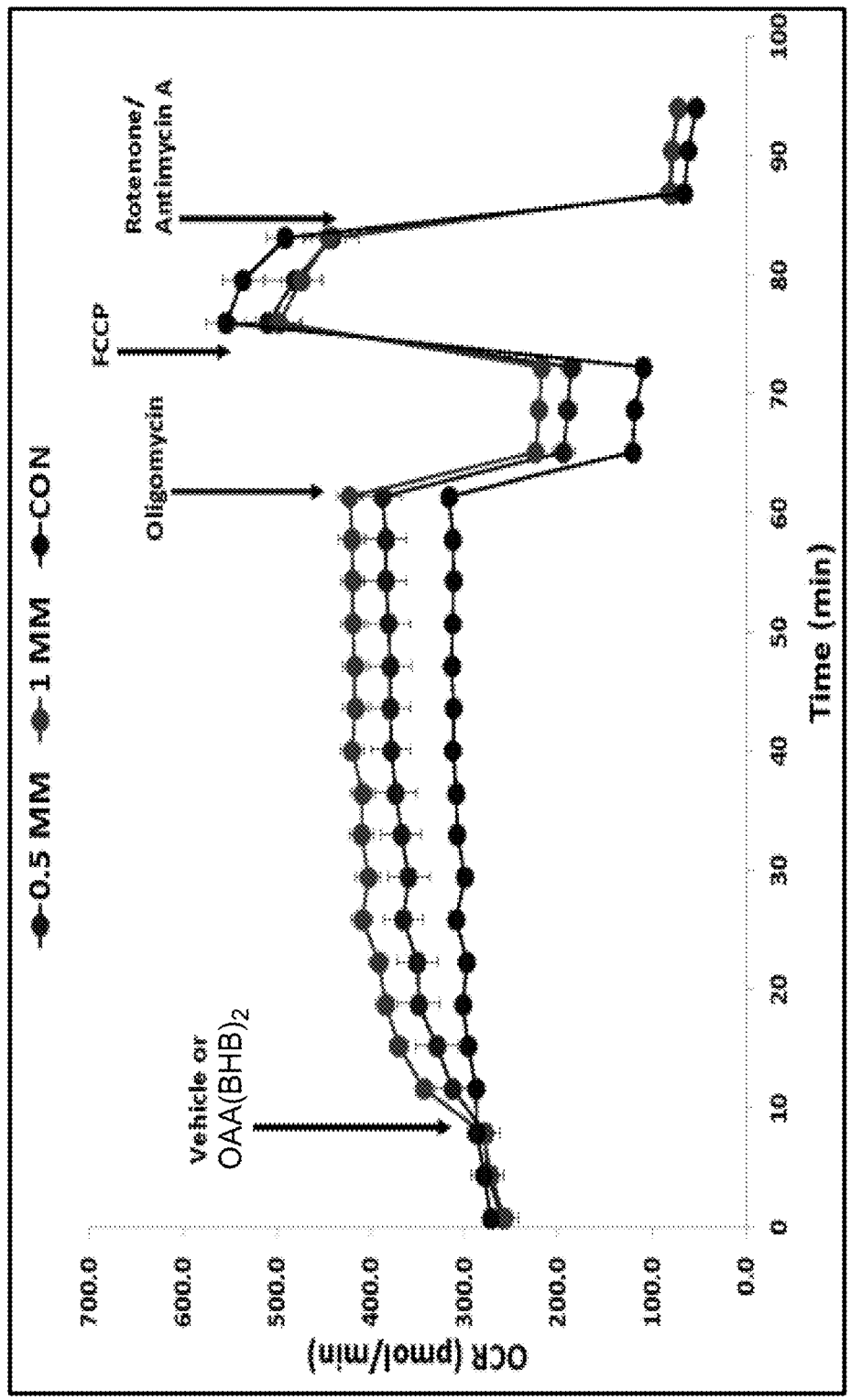
FIG. 2 illustrates that 3,3'-((2-oxosuccinyl)bis(oxy))dibutyric acid) (also referred to herein as "OAA(BHB)$_2$") of the present technology increases SH-SY5Y neuroblastoma cell respiration ~30% at a 1-mM dose, where CON=saline, oligomycin blocks ATP-stimulated respiration, FCCP uncouples respiration (illustrates maximum possible rate), and rotenone/antimycin A are respiratory inhibitors in presence of FCCP. Data are averages of three experiments.
Figure 3A:
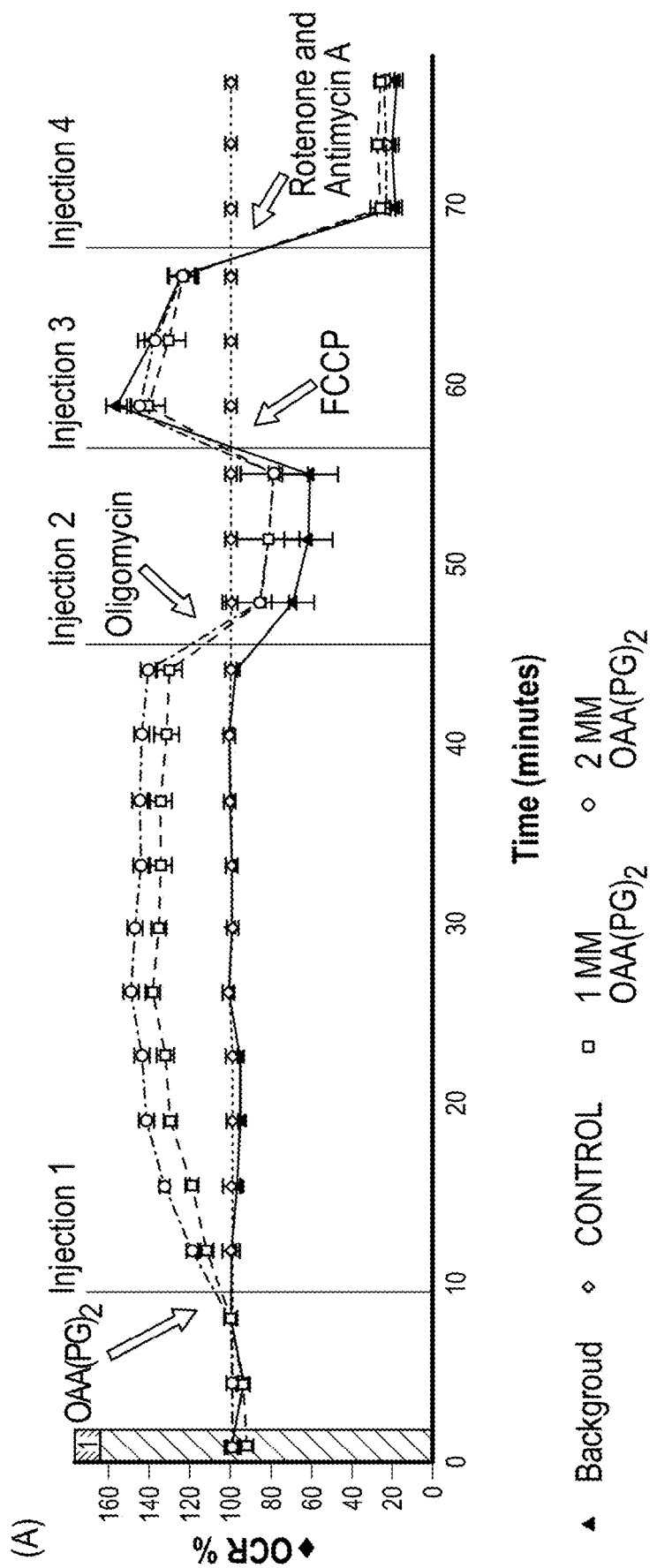
FIGS. 3A-3B illustrate the effect of bis(2-hydroxypropyl) 2-oxosuccinate (also referred to herein as "OAA(PG)$_2$") of the present technology on bioenergetic fluxes, according to the working examples.
Figure 3B:
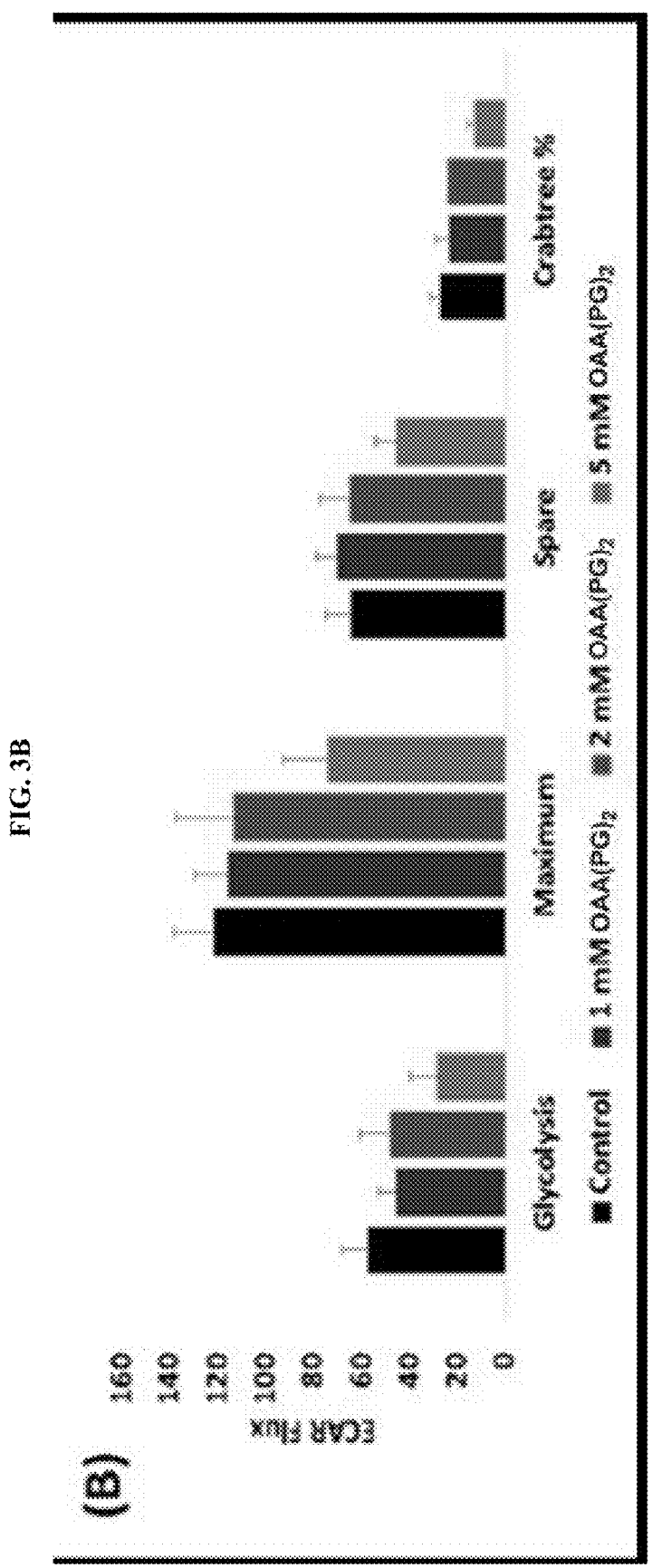
Figure 4:
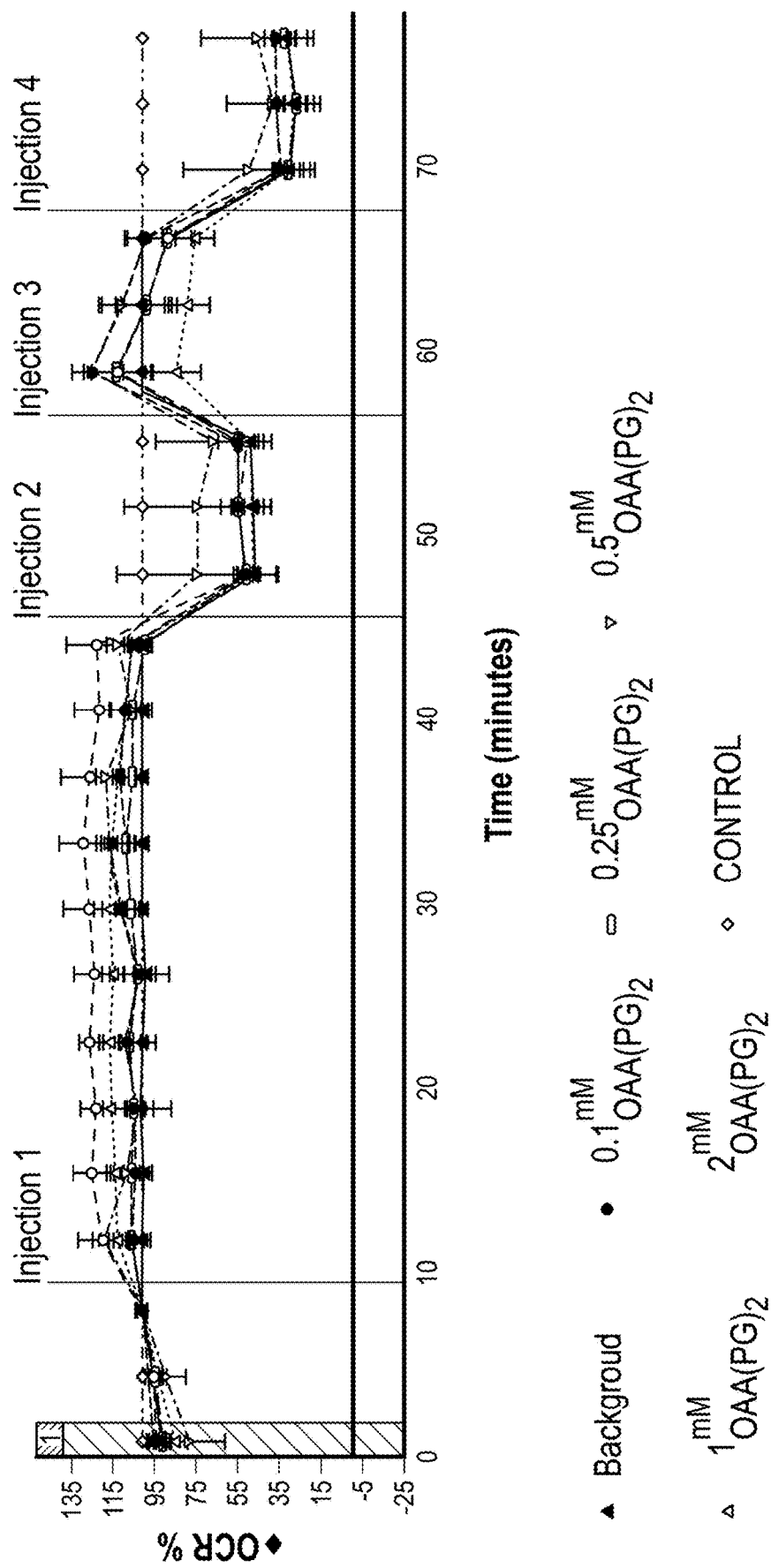
FIG. 4 provides the OCR over time of SH-SY5Y neuroblastoma cells after the addition of differing concentrations OAA(PG)$_2$ in comparison to a control as well as background values, according to the working examples. Data are average of three experiments.

FIG. 2 shows oxygen consumption rates in SH-SY5Y cells acutely exposed to OAA(BHB)$_2$ (compound 1). For these measurements, oligomycin, FCCP, and rotenone/antimycin were used to determine mitochondrial respiration leak rates, the maximum oxygen consumption rate, and the non-mitochondrial oxygen consumption rate. The present studies show that OAA(BHB)$_2$ (compound 1) increases respiration measured as oxygen consumption rate (OCR) when administered to cultured neuronal cells (FIG. 2). In a similar study, OAA(PG)$_2$ (compound 2) was also shown to enhance respiration when administered to cultured neuronal cells (FIGS. 3A and 4). The dose-response was logarithmic over a test range of 0.1 to 2 mM (FIG. 4). FIG. 3A illustrates respiration peaking at ~40% enhancement, which is the maximum possible when mitochondria are chemically uncoupled. FIG. 3B shows glycolysis flux data from OAA (PG)$_2$-treated cells, in which oligomycin is used to switch from the baseline glycolysis flux rate to the maximal glycolysis flux rate; the spare rate is the difference between the basal and maximal rates. FIG. 4 shows Seahorse-determined oxygen consumption rates from SH-SY5Y cells treated with different doses of OAA(PG)$_2$. In FIG. 4 injection 1 is the OAA(PG)$_2$, injection 2 is oligomycin, injection 3 is FCCP, and injection 4 is a rotenone-antimycin mixture. Table 1 below tabulates the percent change in oxygen consumption rate (OCR) upon addition of various concentrations of OAA(PG)$_2$.

TABLE 1

% change in OCR post injection (1) of FIG. 4, average of three experiments

|  | 0.1 mM | 0.25 mM | 0.5 mM | 1 mM | 2mM | Control |
| --- | --- | --- | --- | --- | --- | --- |
| Change in OCR | 101.67755% | 101.11920% | 103.92563% | 106.50295% | 119.75569% | 102.88139% |
| Post-Oligomycin (Leak Rate) | 51.57940% | 50.46191% | 59.14762% | 53.80086% | 50.86488% | 50.66787% |
| Maximum | 98.92179% | 93.08138% | 93.61988% | 81.45515% | 91.73467% | 100.49285% |
| ATP-linked Respiration | 50.09815% | 50.65730% | 44.77801% | 52.70209% | 68.89081% | 52.21351% |

Thus, this Example evidences that OAA(BHB)$_2$ and OAA(PG)$_2$ increased cellular respiration and/or glycolysis to near maximum possible levels (40%, similar to the maximum rate possible when mitochondria are uncoupled by FCC) during preliminary testing (FIGS. 2 and 3).

Furthermore, preliminary testing on D,D and L,L enantiomers of OAA(BHB)$_2$ showed the OAA(D-BHB)$_2$ enantiomer to be significantly more active than the OAA(L-BHB)$_2$ enantiomer, or the racemic mixture.

Overall, these data reveal that: (1) OAA can increase the cell NAD+/NADH ratio, (2) OAA can concomitantly increase aspects of mitochondrial respiration flux and glycolysis flux without uncoupling mitochondrial respiration, (3) that OAA(BHB)$_2$ increases respiration flux, (4) that OAA(PG)$_2$ at concentrations up to 5 mM increases mitochondrial respiration without concomitantly creating a statistical reduction in the glycolysis flux.

Example 3: PK and Distribution Data of OAA(PG)$_2$ and OAA(BHB)$_2$ in Mice

The whole blood, plasma, and brain levels of OAA(BHB)$_2$ and OAA(PG)$_2$ in a laboratory animal will be determined. Administration of OAA(BHB)$_2$ and/or OAA(PG)$_2$ is expected to provide reduced markers of brain inflammation markers. Also expected are altered brain bioenergetic infrastructures, including (but not limited to) one or more of: (i) changes in mitochondrial biogenesis signaling, (ii) mitophagy pathway activation, (iii) changes in oxidative stress, and (iv) changes in insulin signaling. Administration of OAA(BHB)$_2$ and/or OAA(PG)$_2$ is also expected to provide changes in hippocampal neurogenesis activity.

Method: Adult C57Bl/6 mice will be dosed with OAA(BHB)$_2$ and OAA(PG)$_2$. Administration routes will include oral gavage, IP injection, and administration of chow containing 30% of calories as OAA(BHB)$_2$ or OAA(PG)$_2$. PK of the pro-drugs and their active products, OAA and BHB, or OAA and PG, will proceed along similar lines as described in Swerdlow, R. H. et al. Tolerability and Pharmacokinetics of Oxaloacetate 100 mg Capsules in Alzheimer's Subjects. BBA-Clin 2016; 5:120-123, as well as described herein. OAA levels, levels of OAA(BHB)$_2$, levels of OAA(PG)$_2$, BHB analyte, and PG analyte will be measured in whole blood and plasma. Key features in this development and validation will be the determination of stability of the pro-drug and the products in whole blood and in plasma. The method validation and stability studies and all analyses of experimental samples will proceed in compliance with Good Laboratory Practices (GLP).

In order to measure brain levels, a subset of mice will receive deuterated OAA(BHB)$_2$ or deuterated OAA(PG)$_2$. Deuterated PG is commercially available and thus does not require specialized synthesis. Deuterated OAA will by prepared by Cambridge Isotope Laboratories and used in the synthesis of compounds.

Mice will be dosed orally (via gavage) or by IP injection with OAA(BHB)$_2$ or OAA(PG)$_2$ over a range from 100 to 2,000 mg/kg body weight. Duplicate animals will be euthanized at 5, 30, 60, 120, and 240 minutes and blood will be obtained by cardiac puncture and placed in heparinized tubes. Samples will immediately be placed on ice. Plasma will be prepared by centrifugation and transferred to cryovials. Samples will be frozen and stored at −70° C. until analysis. Measured plasma concentrations will be used for non-compartmental PK calculations, with the resulting PK parameters used to guide additional pre-clinical studies with OAA(BHB)$_2$ and OAA(PG)$_2$. Table 2 tabulates the strategy to be used for the IP and gavage conditions.

TABLE 2

PK strategy and use of mice for IP and gavage PK experiments. Two mice (1 male, 1 female) will be used to generate each data point. Each evaluated condition requires 40 mice. 2 compounds (OAA(BHB)$_2$ and OAA(PG)$_2$) will be tested, each at 4 different amounts (100, 500, 1,000, and 2,000 mg/kg body weight). The IP and gavage PK experiments will therefore require (40 mice × 4 conditions) × (2 compounds) = 320 mice.

|  |  | Intraperitoneal Administration | | Gavage Administration | |
| --- | --- | --- | --- | --- | --- |
| Condition: | | Non-Deuterated | Deuterated | Non-Deuterated | Deuterated |
| TIME: | 5 minutes | 2 mice | 2 mice | 2 mice | 2 mice |
|  | 30 minutes | 2 mice | 2 mice | 2 mice | 2 mice |
|  | 60 minutes | 2 mice | 2 mice | 2 mice | 2 mice |
|  | 120 minutes | 2 mice | 2 mice | 2 mice | 2 mice |
|  | 240 minutes | 2 mice | 2 mice | 2 mice | 2 mice |

In addition to the 320 mice indicated in Table 2, chow PK studies will utilize 8 mice (2 consuming deuterated and two consuming non-deuterated OAA(BHB)$_2$ chow, and 2 consuming deuterated and two consuming non-deuterated OAA(PG)$_2$ chow). Also, not shown in Table 2 are two mice that will not receive any of the compounds, and which will serve as control mice. Therefore, PK studies will utilize 330 mice at minimum.

Example 4: Brain Target Engagement with OAA(BHB)$_2$ and OAA(PG)$_2$

Brains from mice treated with OAA show activation of proteins that mediate mitochondrial biogenesis, enhanced insulin signaling pathway activity, reduced neuroinflammation, and increased hippocampal neurogenesis.[5] See Example 3, supra. Brains from mice treated with lactate show increased mitochondrial biogenesis-promoting transcription factor levels, and increased expression of the vascular endothelial growth factor (VEGF) that also functions as a neurotrophic factor.[6] Brains from mice on a ketogenic diet (KD) show alterations in bioenergetics-related gene expression and reduced tumor necrosis factor alpha (TNFα) expression.[7] Human Alzheimer's disease (AD) participants placed on a KD showed improved cognition.[8] This example will determine the effect of OAA(BHB)$_2$ and OAA(PG)$_2$ on brain bioenergetic infrastructures, insulin signaling, neuroinflammation, and hippocampal neurogenesis.

Methods: Five-month old C57BL/6 mice will be divided into three treatment groups, a vehicle-only control group, a 2 g/kg/day OAA(BHB)$_2$ group, and a 2 g/kg/day OAA(PG)$_2$ group. The interventions will be administered IP. The treatment period will last two weeks. Calculations based on a Satterthwaite t-test with a 0.05 one-sided significance level indicates 13 mice per group gives the ability to detect 30% differences with 30% standard deviations at 80% power. Adding three mice to each group will ensure unanticipated morbidity does not excessively diminish power. Table 3 tabulates the treatment strategy to be used for the experiments.

TABLE 3

Treatment strategy and use of mice for Example 4. Sixteen mice (8 male, 8 female) will be used to generate each group. The three groups (control, 2 g/kg/day OAA(BHB)$_2$, and 2 g/kg/day OAA(PG)$_2$) will therefore require a total of 48 mice.

| Vehicle Only | 2 g/kg/day OAA(BHB)$_2$ | 2 g/kg/day OAA(PG)$_2$ |
|---|---|---|
| 16 mice | 16 mice | 16 mice |

Immunochemistry and qPCR will be used to assess proteins and pathways that mediate mitochondrial biogenesis and are sensitive to bioenergetic fluxes. Detailed descriptions of such methods are described in the art.[5, 9] The analysis will characterize PGC1α, AMPK, SIRT1, mTOR, FOXO1A (FKHR), and CREB proteins.[10-15] Effects on AKT, glycogen synthase kinase 3β (GSK3B), and P70SK6 will be determined as measures of insulin pathway signaling. To ascertain effects on neuroinflammation JNK, NFκB, and TNFα will be assessed. To assess hippocampal neurogenesis, hippocampal doublecortin levels will be measured, and a hippocampal immunohistochemical analysis will be performed of the dentate gyrus following doublecortin staining.[5] Group means will be compared by one-way analysis of variance (ANOVA) followed by a Least Significant Difference (LSD) post hoc multiple comparisons test. p values less than 0.05 will be considered significant.

For both compounds, 2 g/kg/day for two weeks will be the starting dosing schedule because with OAA alone, 1 g/kg/day and 2 g/kg/day both induced unequivocal brain changes, and both doses were well-tolerated. In the event that clear pharmacodynamic (PD) changes do not manifest, a brief, acute study will be performed to estimate the maximum tolerable dose (MTD) of the investigational compounds by titrating upwards the amount of compound administered. Once an MTD has been determined, a high dose of the respective compound will be used in the PD studies.

Determining whether a parameter changes will be straightforward. It is possible that for parameters with more than one assessment inconsistencies could arise. For example, phosphorylation but not total levels might change for a given protein. By considering the overall pattern of changes, a reasonably accurate picture of how the compounds affect brain bioenergetics-related physiology will be assembled.

Recently a procedure was developed by the inventors in which brains were dissociated into cell suspensions, and then fluorescence activated cell sorting (FACS) was used to generate markedly enriched, cell specific populations. Enriched cell fractions include neurons, astrocytes, and microglia. RNA was then isolated from the different cell fractions for either targeted or RNASeq analysis. Detecting conflicting changes for a pathway or process could reflect physiologic changes that play out differently in different cell types, for example between neurons and astrocytes. If necessary, this FACS-driven procedure will be used to confirm or refute the possibility of inconsistencies.

Example 5: OAA(D-BHB) Increases Plasma BHB Levels

Figure 5A:
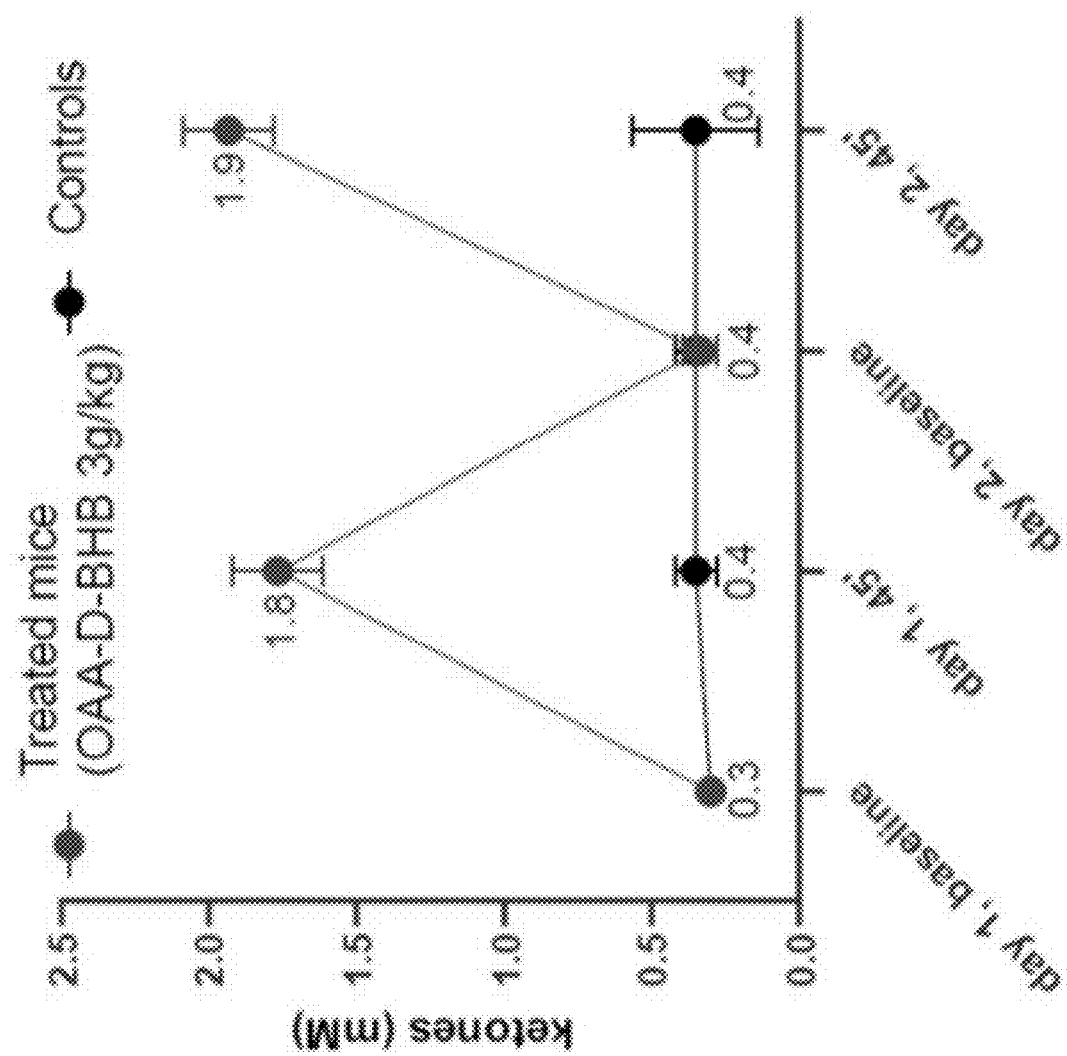
FIGS. 5A-5B show OAA(D-BHB)$_2$ (referred to as "OAA-D-BHB" in these figures) increases plasma BHB levels.
Figure 5B:
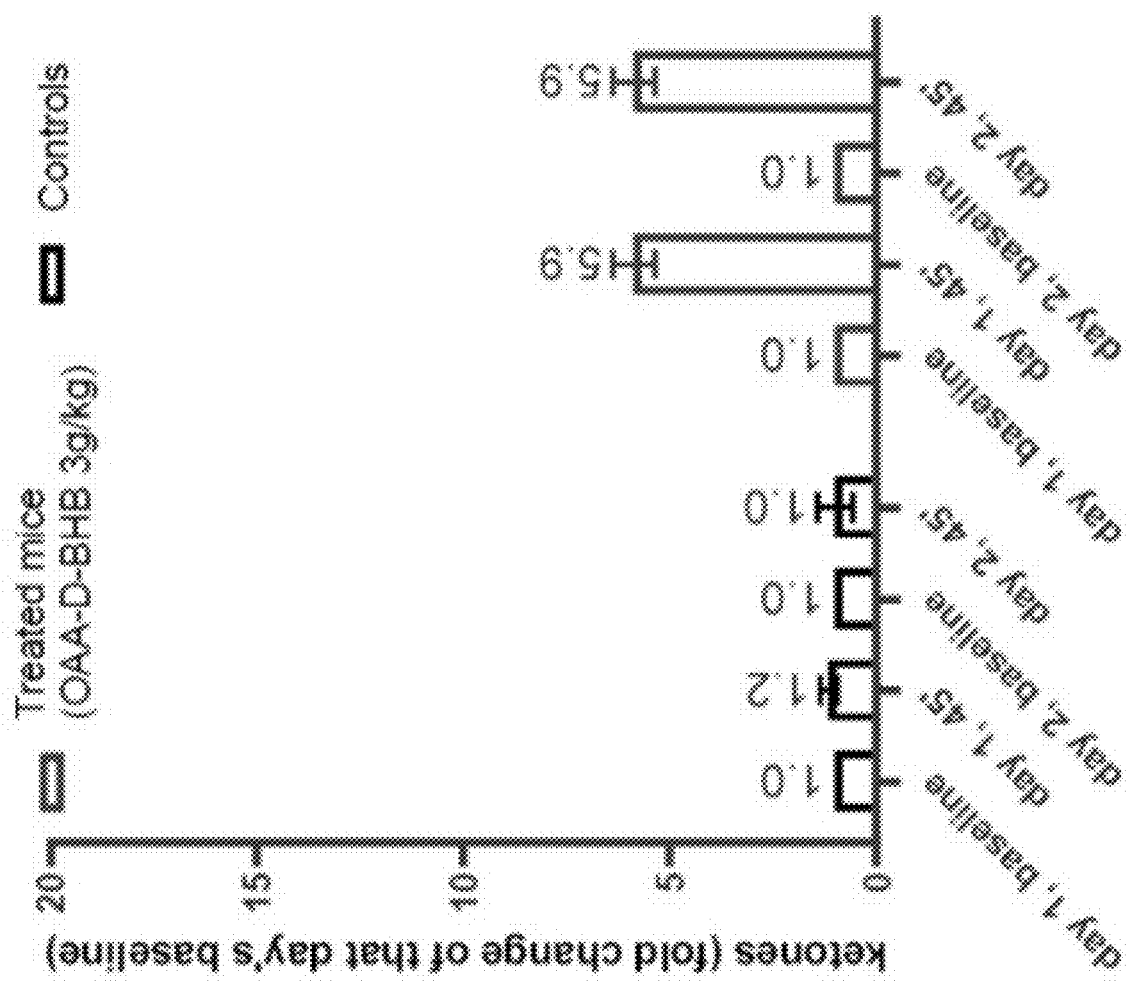

Mice were injected intraperitoneally with OAA(D-BHB)$_2$ at 3 g/kg or with vehicle. Plasma BHB levels were measured just before and again 45 minutes after injection, revealing an approximately 6-fold increase in plasma BHB levels via administration of OAA(BHB)$_2$, as illustrated in FIGS. 5A-5B.

Example 6: Tolerability of OAA(D-BHB)$_2$

Figure 6A:
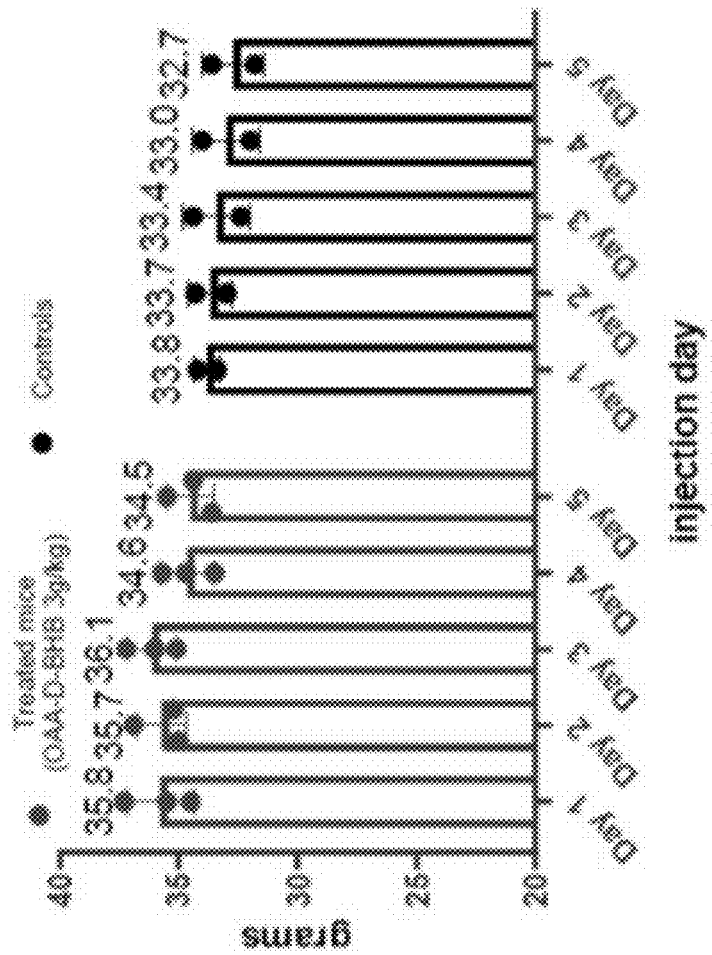
FIGS. 6A-6B show the tolerability of OAA(D-BHB)$_2$ (referred to as "OAA-D-BHB" in these figures) in mice.
Figure 6B:
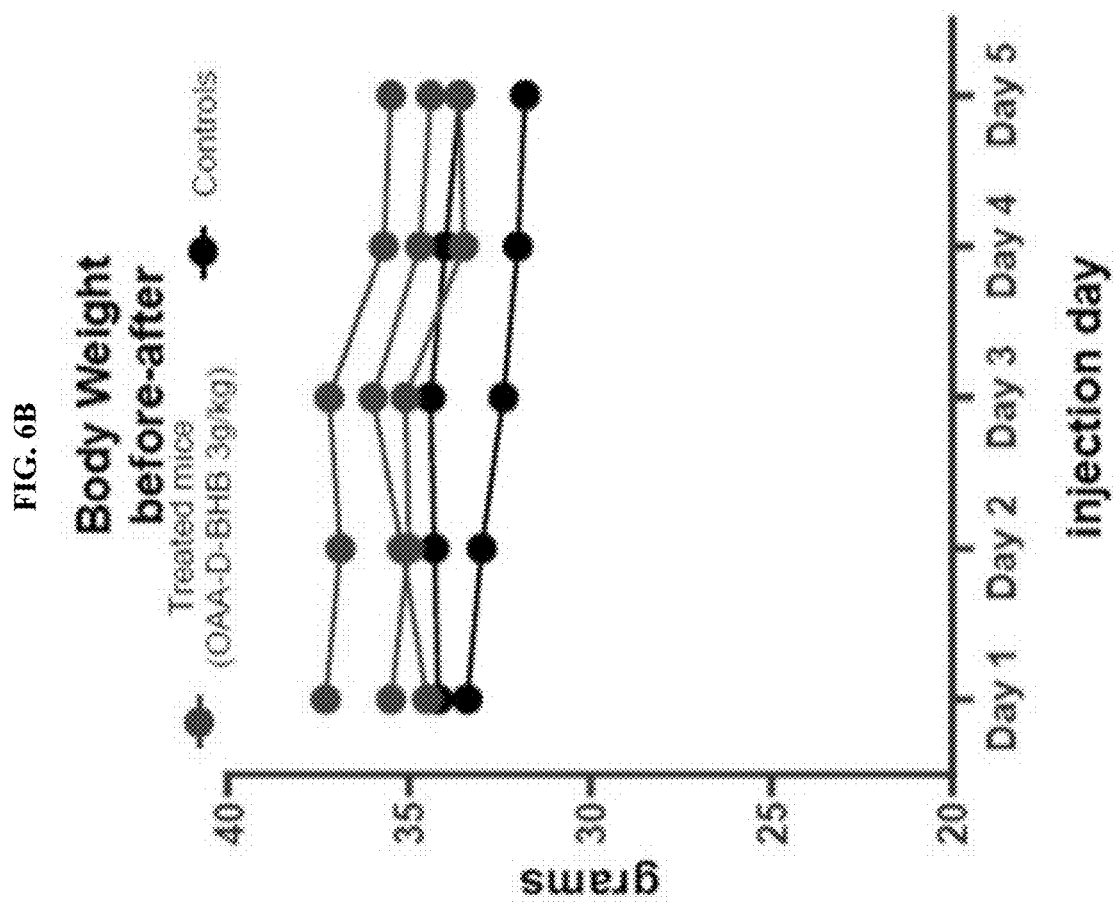

Mice were injected intraperitoneally with OAA(D-BHB)$_2$ at 3 g/kg or with vehicle and weights were measured on days 1-5. Weights remained stable and all mice tolerated the treatment over successive days, as illustrated in FIGS. 6A-6B.

Example 7: Effect of OAA(D-BHB)$_2$ as Compared to Racemic OAA(BHB)$_2$ on Oxygen Consumption Rate Human SH-SY5Y neuronal cells were cultured in various concentrations of the disodium salt of OAA(D-BHB)$_2$ vs racemic mixture of the disodium salt of OAA(BHB)$_2$ (the "racemic salt"), and respiration characterized using a Seahorse Extracellular Flux analyzer (see supra). The disodium salt of OAA(D-BHB)$_2$ enhanced respiration to a greater extent than the racemic salt, as illustrated in FIG. 7.

REFERENCES

1. Chang S W, Zhang D, Chung H D, Zassenhaus H P. The frequency of point mutations in mitochondrial DNA is elevated in the Alzheimer's brain. Biochem Biophys Res Commun. 2000; 273(1):203-8. Epub 2000 Jun. 30. PubMed PMID: 10873587.
2. Coskun P E, Beal M F, Wallace D C. Alzheimer's brains harbor somatic mtDNA control-region mutations that suppress mitochondrial transcription and replication. Proceedings of the National Academy of Sciences of the United States of America. 2004; 101(29):10726-31. Epub 2004 Jul. 13. PubMed PMID: 15247418; PMCID: 490002.
3. Coskun P E, Wyrembak J, Derbereva O, Melkonian G, Doran E, Lott I T, Head E, Cotman C W, Wallace D C. Systemic mitochondrial dysfunction and the etiology of Alzheimer's disease and down syndrome dementia. Journal of Alzheimer's disease: JAD. 2010; 20 Suppl 2:S293-310. Epub 2010 May 14. PubMed PMID: 20463402.
4. Gasior M, Rogawski M A, Hartman A L. Neuroprotective and disease-modifying effects of the ketogenic diet. Behav Pharmacol. 2006; 17(5-6):431-9. Epub 2006 Aug. 31. PubMed PMID: 16940764; PMCID: 2367001.
5. Wilkins H M, Harris J L, Carl S M, E L, Lu J, Eva Selfridge J, Roy N, Hutfles L, Koppel S, Morris J, Burns J M, Michaelis M L, Michaelis E K, Brooks W M, Swerdlow R H. Oxaloacetate activates brain mitochondrial biogenesis, enhances the insulin pathway, reduces inflammation and stimulates neurogenesis. Human molecular genetics. 2014; 23(24):6528-41. Epub 2014 Jul. 17. PubMed PMID: 25027327.
6. E L, Lu J, Selfridge J E, Burns J M, Swerdlow R H. Lactate administration reproduces specific brain and liver exercise-related changes. Journal of neurochemistry 2013; 127:91-100.
7 Selfridge J E, Wilkins H M, E L, et al. Effect of one month duration ketogenic and non-ketogenic high fat diets on mouse brain bioenergetic infrastructure. J Bioenerg Biomembr 2015; 47:1-11.
8. Taylor M K, Sullivan D K, Mahnken D J, Burns J M, Swerdlow R H. Feasibility and efficacy data from a ketogenic diet intervention in Alzheimer disease. Alzheimer Dement TRCI, in press.
9. Lu J, E L, Wang W, et al. Alternate day fasting impacts the brain insulin-signaling pathway of young adult male C57BL/6 mice. J Neurochem 2011: Epub ahead of print.
10. Cunningham J T, Rodgers J T, Arlow D H, Vazquez F, Mootha V K, Puigserver P. mTOR controls mitochondrial oxidative function through a YY1-PGC-1alpha transcriptional complex. Nature 2007; 450:736-740.
11. Daitoku H, Yamagata K, Matsuzaki H, Hatta M, Fukamizu A. Regulation of PGC-1 promoter activity by protein kinase B and the forkhead transcription factor FKHR. Diabetes 2003; 52:642-649.
12. Herzig S, Long F, Jhala U S, et al. CREB regulates hepatic gluconeogenesis through the coactivator PGC-1. Nature 2001; 413:179-183.
13. Nakae J, Oki M, Cao Y. The FoxO transcription factors and metabolic regulation. FEBS Lett 2008; 582:54-67.
14. Schieke S M, Phillips D, McCoy J P, Jr., et al. The mammalian target of rapamycin (mTOR) pathway regulates mitochondrial oxygen consumption and oxidative capacity. The Journal of biological chemistry 2006; 281: 27643-27652.
15. Wu Z, Huang X, Feng Y, et al. Transducer of regulated CREB-binding proteins (TORCs) induce PGC-1alpha transcription and mitochondrial biogenesis in muscle cells. Proceedings of the National Academy of Sciences of the United States of America 2006; 103:14379-14384.

While certain embodiments have been illustrated and described, a person with ordinary skill in the art, after reading the foregoing specification, can effect changes, substitutions of equivalents and other types of alterations to the compounds of the present technology or salts, pharmaceutical compositions, derivatives, prodrugs, metabolites, tautomers or racemic mixtures thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present technology may include, but is not limited to, the features and combinations of features recited in the following lettered paragraphs, it being understood that the following paragraphs should not be interpreted as limiting the scope of the claims as appended hereto or mandating that all such features must necessarily be included in such claims:

A. A compound of Formula I

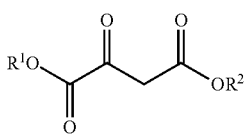
(I)

or a pharmaceutically acceptable salt and/or solvate thereof,
wherein $R^1$ and $R^2$ are each independently
H,

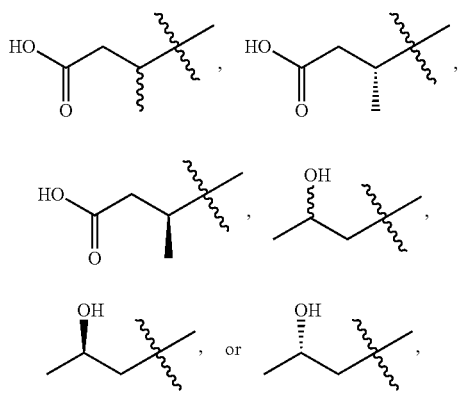

provided that at least one of $R^1$ and $R^2$ is not H.

B. The compound of Paragraph A, wherein both $R^1$ and $R^2$ are

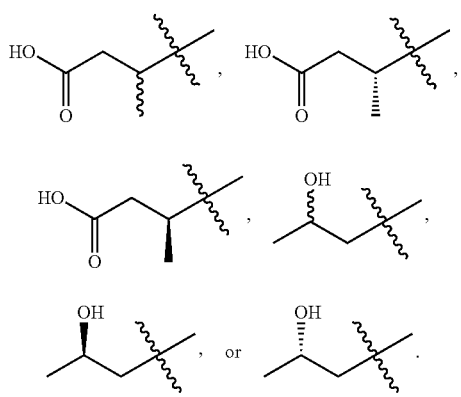

C. The compound of Paragraph A or Paragraph B, wherein the compound of Formula I is

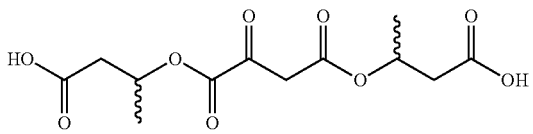

or a pharmaceutically acceptable salt and/or solvate thereof;

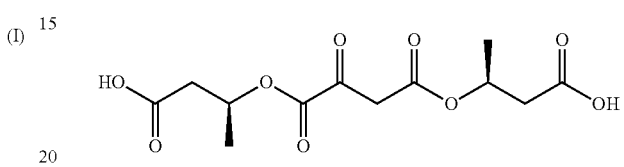

or a pharmaceutically acceptable salt and/or solvate thereof;

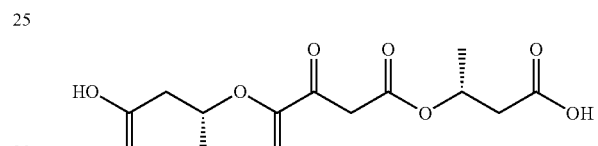

or a pharmaceutically acceptable salt and/or solvate thereof;

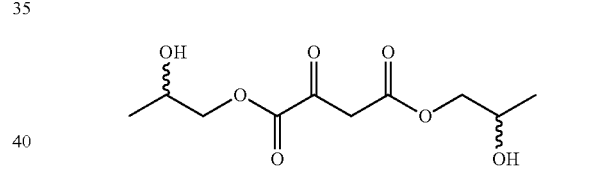

or a pharmaceutically acceptable salt and/or solvate thereof;

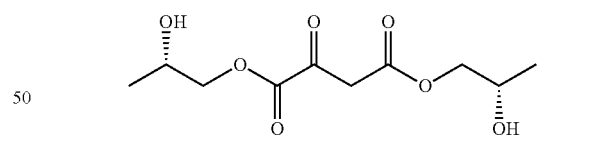

or a pharmaceutically acceptable salt and/or solvate thereof; or

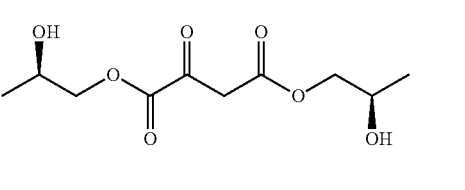 [SMILES: C[C@@H](O)COC(=O)CC(=O)C(=O)OC[C@@H](C)O]

or a pharmaceutically acceptable salt and/or solvate thereof.

D. The compound of any one of Paragraphs A-C, wherein the compound of Formula I is

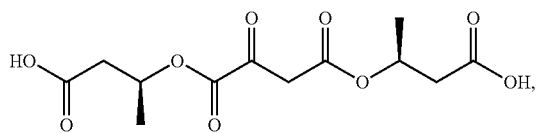 [SMILES: C[C@@H](CC(=O)O)OC(=O)CC(=O)C(=O)O[C@@H](C)CC(=O)O]

a potassium salt of

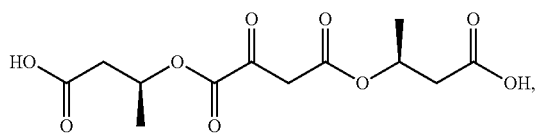 [SMILES: C[C@@H](CC(=O)O)OC(=O)CC(=O)C(=O)O[C@@H](C)CC(=O)O]

a dipotassium salt of

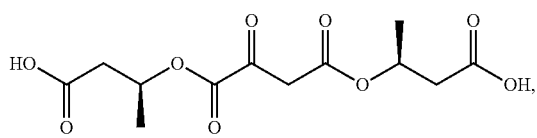 [SMILES: C[C@@H](CC(=O)O)OC(=O)CC(=O)C(=O)O[C@@H](C)CC(=O)O]

a sodium salt of

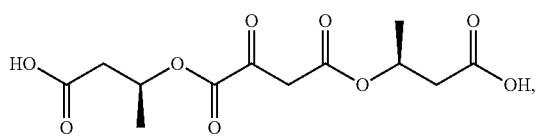 [SMILES: C[C@@H](CC(=O)O)OC(=O)CC(=O)C(=O)O[C@@H](C)CC(=O)O]

a disodium salt of

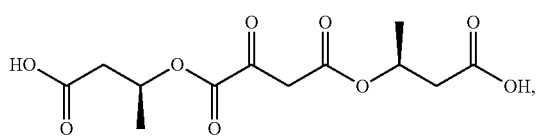 [SMILES: C[C@@H](CC(=O)O)OC(=O)CC(=O)C(=O)O[C@@H](C)CC(=O)O]

a sodium potassium salt of or a solvate thereof of any one of these.

E. A pharmaceutical composition comprising a compound of any one of Paragraphs A-D; and a pharmaceutically acceptable carrier.

F. A pharmaceutical composition comprising an effective amount of a compound of any one of Paragraphs A-D; and a pharmaceutically acceptable carrier.

G. The pharmaceutical composition of Paragraph F, wherein the effective amount is an amount of the compound effective to increase cellular respiration and/or glycolytic flux in a subject.

H. The pharmaceutical composition of Paragraph F or Paragraph G, wherein the effective amount is an amount effective to treat a neurodegenerative disease in a subject.

I. The pharmaceutical compounds of any one of Paragraphs F-H, wherein the effective amount is an amount effective to treat Alzheimer's disease in a subject.

J. The pharmaceutical composition of any one of Paragraphs F-I, wherein the effective amount is an amount effective to treat Parkinson's disease in a subject.

K. The pharmaceutical composition of any one of Paragraphs F-J, wherein the effective amount is an amount effective to treat amyotrophic lateral sclerosis in a subject.

L. The pharmaceutical composition of any one of Paragraphs F-K, wherein the effective amount is an amount effective to treat multiple sclerosis in a subject.

M. The pharmaceutical composition of any one of Paragraphs F-L, wherein the effective amount is an amount effective to treat epilepsy in a subject.

N. The pharmaceutical composition of any one of Paragraphs F-M, wherein the effective amount is an amount effective to treat a mitochondrial disorder in a subject.

O. The pharmaceutical composition of any one of Paragraphs F-N, wherein the effective amount is an amount effective to improve athletic performance in a subject.

P. The pharmaceutical composition of any one of Paragraphs F-O, wherein the effective amount is an amount effective to improve cognitive performance in a subject.

Q. A method for increasing cellular respiration in a cell, the method comprising contacting the cell with a compound of any one of Paragraphs A-D.

R. The method of Paragraph O, wherein the cell is a neuronal cell.

S. A method of increasing a ratio of cytosolic $NAD^+$ to NADH in a cell, the method comprising contacting the cell with a compound of any one of Paragraphs A-D.

T. The method of Paragraph S, wherein the cell is a neuronal cell.

U. A method of increasing glycolytic flux in a cell, the method comprising contacting the cell with a compound of any one of Paragraphs A-D.

V. The method of Paragraph U, wherein the cell is a neuronal cell.

W. A method of increasing cellular respiration in a subject, the method comprising administering to the subject an effective amount of a compound of any one of Paragraphs A-D.

X. The method of Paragraph W, wherein the subject is suffering from a neurodegenerative disease.

Y. The method of Paragraph W or Paragraph X, wherein the neurodegenerative disease comprises Alzheimer's disease.

Z. The method of any one of Paragraphs W-Y, wherein the effective amount is an amount effective to treat Alzheimer's disease.

AA. The method of any one of Paragraphs W-Z, wherein the neurodegenerative disease comprises Parkinson's disease.

AB. The method of any one of Paragraphs W-AA, wherein the effective amount is an amount effective to treat Parkinson's disease.

AC. The method of any one of Paragraphs W-AB, wherein the subject is suffering from amyotrophic lateral sclerosis.

AD. The method of any one of Paragraphs W-AC, wherein the effective amount is an amount effective to treat amyotrophic lateral sclerosis.

AE. The method of any one of Paragraphs W-AD, wherein the subject is suffering from multiple sclerosis.

AF. The method of any one of Paragraphs W-AE, wherein the effective amount is an amount effective to treat multiple sclerosis.

AG. The method of any one of Paragraphs W-AF, wherein the subject is suffering from epilepsy.

AH. The method of any one of Paragraphs W-AG, wherein the effective amount is an amount effective to treat epilepsy.

AI. A method of increasing glycolytic flux in a subject, the method comprising administering to the subject an effective amount of a compound of any one of Paragraphs A-D.

AJ. The method of Paragraph AI, wherein the subject is suffering from a neurodegenerative disease.

AK. The method of Paragraph AI or Paragraph AJ, wherein the neurodegenerative disease comprises Alzheimer's disease.

AL. The method of any one of Paragraphs AI-AK, wherein the effective amount is an amount effective to treat Alzheimer's disease.

AM. The method of any one of Paragraphs AI-AL, wherein the neurodegenerative disease comprises Parkinson's disease.

AN. The method of any one of Paragraphs AI-AM, wherein the effective amount is an amount effective to treat Parkinson's disease.

AO. The method of any one of Paragraphs AI-AN, wherein the subject is suffering from amyotrophic lateral sclerosis.

AP. The method of any one of Paragraphs AI-AO, wherein the effective amount is an amount effective to treat amyotrophic lateral sclerosis.

AQ. The method of any one of Paragraphs AI-AP, wherein the subject is suffering from multiple sclerosis.

AR. The method of any one of Paragraphs AI-AQ, wherein the effective amount is an amount effective to treat multiple sclerosis.

AS. The method of any one of Paragraphs AI-AR, wherein the subject is suffering from epilepsy.

AT. The method of any one of Paragraphs AI-AS, wherein the effective amount is an amount effective to treat epilepsy.

AU. A method of treating a subject suffering from a neurodegenerative disease, the method comprising administering an effective amount of a compound of any one of Paragraphs A-D to the subject.

AV. The method of Paragraph AU, wherein the neurodegenerative disease comprises Alzheimer's disease.

AW. The method of Paragraph AU or Paragraph AV, wherein the effective amount is an amount effective to treat Alzheimer's disease.

AX. The method of any one of Paragraphs AU-AW, wherein the neurodegenerative disease comprises Parkinson's disease.

AY. The method of any one of Paragraphs AU-AX, wherein the effective amount is an amount effective to treat Parkinson's disease.

AZ. The method of any one of Paragraphs AU-AY, wherein the neurodegenerative disease comprises amyotrophic lateral sclerosis.

BA. The method of any one of Paragraphs AU-AZ, wherein the effective amount is an amount effective to treat amyotrophic lateral sclerosis.

BB. A method for increasing ketone levels in a subject, the method comprising administering to the subject a compound of any one of Paragraphs A-D.

BC. The method of Paragraph BB, wherein the method comprises administering to the subject an effective amount of the compound, wherein the effective amount is an amount that increases ketone levels in the subject.

BD. The method of Paragraph BB or Paragraph BC, wherein increasing ketone levels in the subject comprises increasing ketone levels in blood of the subject by administering the compound.

BE. The method of any one of Paragraphs BB-BD, wherein increasing ketone levels in the subject comprises increasing ketone levels in plasma of the subject by administering the compound.

BF. The method of any one of Paragraphs BB-BE, wherein increasing ketone levels in the subject comprises increasing ketogenesis in the subject by administering the compound.

BG. The method of any one of Paragraphs BB-BF, wherein increasing ketone levels in the subject comprises an increase of ketones derived from administering the compound.

BH. A method of treating a subject suffering from multiple sclerosis, the method comprising administering an effective amount of a compound of any one of Paragraphs A-D to the subject, wherein the effective amount is an amount effective to treat multiple sclerosis.

BI. A method of treating a subject suffering from epilepsy, the method comprising administering an effective amount of a compound of any one of Paragraphs A-D to the subject, wherein the effective amount is an amount effective to treat epilepsy.

Other embodiments are set forth in the following claims.

What is claimed:
1. A pharmaceutical composition comprising a compound of Formula I

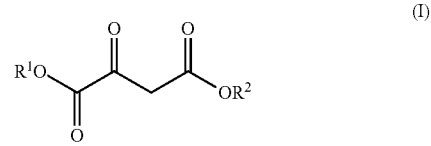

or a pharmaceutically acceptable salt and/or solvate thereof, wherein both $R^1$ and $R^2$ are

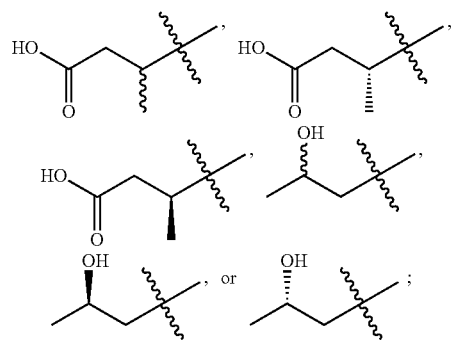

and
a pharmaceutically acceptable carrier.

2. A pharmaceutical composition comprising an effective amount of a compound of Formula I

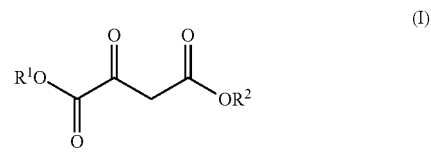

or a pharmaceutically acceptable salt and/or solvate thereof, wherein both $R^1$ and $R^2$ are

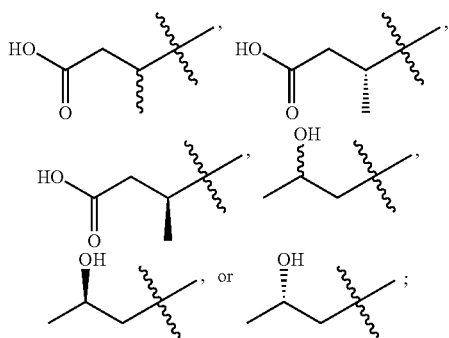

and
a pharmaceutically acceptable carrier.

3. The pharmaceutical composition of claim 2, wherein the effective amount is an amount of the compound effective to increase cellular respiration and/or glycolytic flux in a subject.

4. The pharmaceutical composition of claim 2, wherein the effective amount is an amount effective to treat a neurodegenerative disease in a subject.

5. The pharmaceutical composition of claim 2, wherein the effective amount is an amount effective to treat Alzheimer's disease in a subject.

6. The pharmaceutical composition of claim 2, wherein the effective amount is an amount effective to treat Parkinson's disease in a subject.

7. The pharmaceutical composition of claim 2, wherein the effective amount is an amount effective to treat amyotrophic lateral sclerosis in a subject.

8. The pharmaceutical composition of claim 2, wherein the effective amount is an amount effective to treat multiple sclerosis in a subject.

9. The pharmaceutical composition of claim 2, wherein the effective amount is an amount effective to treat epilepsy in a subject.

10. The pharmaceutical composition of claim 2, wherein the effective amount is an amount effective to treat a mitochondrial disorder in a subject.

11. The pharmaceutical composition of claim 2, wherein the effective amount is an amount effective to improve athletic performance in a subject.

12. The pharmaceutical composition of claim 2, wherein the effective amount is an amount effective to improve cognitive performance in a subject.

13. A method for increasing cellular respiration in a cell, the method comprising contacting the cell with a compound of Formula I

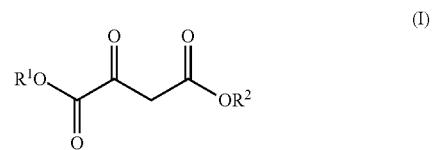

(I)

or a pharmaceutically acceptable salt and/or solvate thereof, wherein both $R^1$ and $R^2$ are

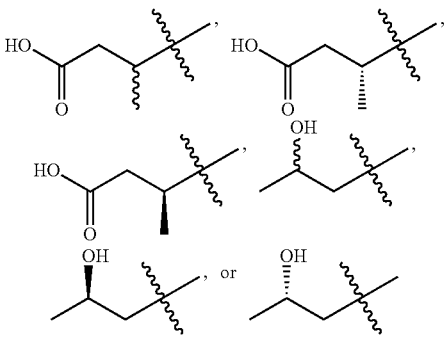

14. The method of claim 13, wherein the cell is a neuronal cell.

* * * * *